US010987624B2

(12) United States Patent
Mueller

(10) Patent No.: US 10,987,624 B2
(45) Date of Patent: Apr. 27, 2021

(54) REMOVAL OF GREENHOUSE GASES AND HEAVY METALS FROM AN EMISSION STREAM

(71) Applicant: ISCA Management Ltd., Vancouver (CA)

(72) Inventor: Barbara Mueller, Vancouver (CA)

(*) Notice: Subject to any disclaimer, the term of this patent is extended or adjusted under 35 U.S.C. 154(b) by 0 days.

(21) Appl. No.: 16/472,494

(22) PCT Filed: Dec. 21, 2017

(86) PCT No.: PCT/CA2017/051580
§ 371 (c)(1),
(2) Date: Jun. 21, 2019

(87) PCT Pub. No.: WO2018/112653
PCT Pub. Date: Jun. 28, 2018

(65) Prior Publication Data
US 2020/0188847 A1 Jun. 18, 2020

Related U.S. Application Data

(60) Provisional application No. 62/437,138, filed on Dec. 21, 2016.

(51) Int. Cl.
B01D 53/75 (2006.01)
B01D 53/56 (2006.01)
(Continued)

(52) U.S. Cl.
CPC ............ B01D 53/75 (2013.01); B01D 53/26 (2013.01); B01D 53/507 (2013.01); B01D 53/56 (2013.01);
(Continued)

(58) Field of Classification Search
CPC combination set(s) only.
See application file for complete search history.

(56) References Cited

U.S. PATENT DOCUMENTS 4,152,217 A 5/1979 Eisenberg et al.
4,477,419 A 10/1984 Pearce et al.
(Continued)

FOREIGN PATENT DOCUMENTS

GB 1593742 7/1981
JP S51 128676 11/1976
(Continued)

OTHER PUBLICATIONS

International Search Report and Written Opinion dated Mar. 28, 2018 in Application No. PCT/CA2017/051580.
(Continued)

Primary Examiner — Ellen M McAvoy
Assistant Examiner — Chantel L Graham
(74) Attorney, Agent, or Firm — Snell & Wilmer L.L.P.

(57) ABSTRACT

The present disclosure relates to a flue gas treatment system (e.g. a multi-pollutant flue gas treatment system) for removal of greenhouse gases such as $SO_2$, NO, $NO_2$, $H_2S$, HCl, water and $CO_2$ as well as heavy metals (e.g. mercury, arsenic, bismuth, cadmium, lead and/or selenium) from the flue gases of fossil-fueled utility and industrial plants by reacting the raw flue gas, firstly, with chlorine in a gas-phase oxidation reaction and recovering the resulting products as marketable products, and then, secondly, treating the cleaned gas, which includes $CO_2$, with a Sabatier reaction to produce a hydrocarbon fuel (e.g. methane). The system also includes an electrolytic unit for electrolyzing HCl to produce hydrogen gas for the Sabatier reaction as well as chlorine gas, which may then be recycled into the reactor.

20 Claims, 2 Drawing Sheets

(51) Int. Cl.

| | | |
|---|---|---|
| *C25B 1/02* | (2006.01) | |
| *C25B 1/26* | (2006.01) | |
| *B01D 53/50* | (2006.01) | |
| *B01D 53/64* | (2006.01) | |
| *B01D 53/26* | (2006.01) | |
| *B01D 53/76* | (2006.01) | |
| *B01D 53/78* | (2006.01) | |
| *C25B 9/06* | (2006.01) | |
| *B01J 19/24* | (2006.01) | |
| *C07C 1/12* | (2006.01) | |
| *C10L 3/08* | (2006.01) | |
| *C10L 1/32* | (2006.01) | |
| *B01D 53/86* | (2006.01) | |

(52) U.S. Cl.
CPC ............. *B01D 53/64* (2013.01); *B01D 53/76* (2013.01); *B01D 53/78* (2013.01); *B01D 53/8671* (2013.01); *B01J 19/24* (2013.01); *C07C 1/12* (2013.01); *C10L 1/322* (2013.01); *C10L 3/08* (2013.01); *C25B 1/02* (2013.01); *C25B 1/26* (2013.01); *C25B 9/06* (2013.01); *B01D 2251/108* (2013.01); *B01D 2257/302* (2013.01); *B01D 2257/404* (2013.01); *B01D 2257/504* (2013.01); *B01D 2257/602* (2013.01); *B01D 2257/80* (2013.01); *C10L 2290/08* (2013.01); *C10L 2290/24* (2013.01); *C10L 2290/42* (2013.01); *C10L 2290/541* (2013.01)

(56) References Cited

U.S. PATENT DOCUMENTS

| | | | |
|---|---|---|---|
| 4,619,608 A * | 10/1986 | McIntyre | ............... B01D 53/34 423/220 |
| 6,447,740 B1 | 9/2002 | Caldwell et al. | |
| 7,056,482 B2 | 6/2006 | Hakia et al. | |
| 8,198,338 B2 | 6/2012 | Shulenberger | |
| 8,227,127 B2 | 7/2012 | Little | |
| 8,747,520 B2 | 6/2014 | Bearden et al. | |
| 8,754,269 B2 | 6/2014 | O'Connor | |
| 9,057,138 B2 | 6/2015 | Stuermer | |
| 9,061,920 B2 | 6/2015 | Pohl et al. | |
| 9,085,497 B2 | 7/2015 | Jennings | |
| 9,090,978 B2 | 7/2015 | Beckett | |
| 9,101,876 B2 | 8/2015 | Atanackovic et al. | |
| 9,133,076 B2 | 9/2015 | Iyer et al. | |
| 9,144,770 B2 | 9/2015 | Liu et al. | |
| 9,193,927 B2 | 11/2015 | Zhang et al. | |
| 9,238,214 B2 | 1/2016 | Livneh | |
| 9,267,211 B2 | 2/2016 | Gilliam et al. | |
| 9,285,116 B2 | 3/2016 | Schmid et al. | |
| 9,315,910 B2 | 4/2016 | Eastman | |
| 9,353,323 B2 | 5/2016 | Kyle | |
| 9,440,189 B2 | 9/2016 | Mercier | |
| 9,481,837 B2 | 11/2016 | Velazquez-Vargas | |
| 9,624,154 B2 | 4/2017 | Blair | |
| 9,758,740 B2 | 9/2017 | Zhang et al. | |
| 9,808,783 B2 | 11/2017 | Shen | |
| 9,937,484 B2 | 4/2018 | Liu | |
| 10,208,665 B2 | 2/2019 | Simpson | |
| 10,227,901 B2 | 3/2019 | Bergins | |
| 10,385,732 B2 | 8/2019 | Fleischer | |
| 10,421,913 B2 | 9/2019 | von Olshausen | |
| 2006/0239877 A1 | 10/2006 | Johnson et al. | |
| 2007/0217982 A1* | 9/2007 | Wright | ............... B01D 53/1493 423/230 |
| 2007/0244208 A1 | 10/2007 | Shulenberger | |
| 2012/0226080 A1 | 9/2012 | Meyer-Pittroff | |
| 2013/0078159 A1 | 3/2013 | Fan et al. | |
| 2013/0202516 A1 | 8/2013 | Jones et al. | |
| 2014/0124379 A1 | 5/2014 | Teamey | |
| 2014/0323600 A1 | 10/2014 | Jennings | |
| 2014/0328743 A1 | 11/2014 | Jones | |
| 2015/0037231 A1 | 2/2015 | Seeker | |
| 2015/0231562 A1 | 8/2015 | Fradette et al. | |
| 2015/0232999 A1 | 8/2015 | Busskamp | |
| 2015/0299873 A1 | 10/2015 | Beckett | |
| 2016/0017800 A1 | 1/2016 | Simpson | |
| 2016/0039724 A1 | 2/2016 | Naterer | |
| 2016/0194766 A1 | 7/2016 | Eastman | |

FOREIGN PATENT DOCUMENTS

| | | |
|---|---|---|
| WO | 1999/058228 | 11/1999 |
| WO | 2006/128326 | 7/2006 |

OTHER PUBLICATIONS

International Preliminary Report on Patentability dated Nov. 6, 2018 in Application No. PCT/CA2017/051580.
Bemand, et al., "Atomic Resonance Fluorescence Spetrometry for Rate Constants of Rapid Bimolecular Reacions," *J. Chem. Soc. Faraday Trans.* 1, 1973, 69: 1356.
Environmental Defense Fund, "Coal-Fired Power Plants are Big Contributors to Sooty Particle Pollution in Eastern States," 2008.
Lunde et al, "Kinetics of Carbon Dioxide Methanation on a Ruthenium Catalyst," *Ind. Eng. Chem. Process Des. Dev.*, 1974, 13(1): 27-33.
Oblad, Alex G., "The Kel-chor Process," Industrial Engineering Chemistry, vol. 61 No. 7 Jul. 1969 23.
Patel, S., "The Big Picture: Energy for Power," *Power*, Apr. 2016, p. 12.
Patel, S., "The Big Picture: Future Coal Fleet," *Power*, Jan. 2016, p. 10.
Ralston, J., "The Sabatier Reaction, Possible Solution to CO2 Emissions". Penn Energy, Mar. 4, 2010 (Apr. 3, 2010), [online] [retrieved on Mar. 25, 2014 (Mar. 25, 2014)]. Retrieved from the Internet: <http://www.pennenergy.com/articles/pennenergy/20 1 0/03/the-sa batier-reaction.html>.
Water Vapor, NOAA National Centers for Environmental Information, https://www.ncdc.noaa.gov/monitoring-references/faq/greenhouse-gases.php, accessed Dec. 14, 2016.
European Search Report dated Jul. 9, 2020 in Application No. 17883522.9.

* cited by examiner

REMOVAL OF GREENHOUSE GASES AND HEAVY METALS FROM AN EMISSION STREAM

CROSS-REFERENCE TO RELATED APPLICATIONS

This application is a U.S. national phase filing under 35 U.S.C. § 371 of PCT/CA2017/051580filed on Dec. 21, 2017 entitled "REMOVAL OF GREENHOUSE GASES AND HEAVY METALS FROM AN EMISSION STREAM," which claims priority to U.S. Provisional Patent Application No. 62/437,138 filed on Dec. 21, 2016, the disclosures of which are incorporated herein by reference.

TECHNICAL FIELD

The present disclosure relates to a system and a method for removing greenhouse gases and other pollutants from emission stream.

BACKGROUND

Flue gas generally refers to the exhaust gas produced by energy generating apparatuses or systems such as, but not limited to, power plants, coal-fired facilities, gas burning facilities, furnaces, boilers, and steam generators. While the ultimate composition of flue gas depends on the nature of the products being combusted in the energy generating apparatus or system, flue gas generally contains greenhouse gas compounds such as, but not limited to, sulfur oxides, nitrogen oxides, carbon dioxide, carbon monoxide, and water vapour, and other pollutants such as, but not limited to, hydrogen sulfide, heavy metals (e.g. mercury), soot, dust, smoke, and hazardous trace elements.

According to a survey administered by the Energy Information Administration (the "EIA") of 1900 power facilities in the United States of America, the power production distributions provided below were observed in 2015[1]:

TABLE 1

| Production Method | Percentage of overall Power Generation |
|---|---|
| Coal-fired combustion | About 35% |
| Gas-fired combustion | About 27% |
| Nuclear | About 21% |
| Hydro | About 6% |
| Wind | About 5% |
| Others including wood/ wood waste, solar, geothermal, bio-gas consumption, etc . . . | Each about 1% or less |

On a global perspective, the International Energy Agency (the "IEA") recently estimated that nearly a third of the world's currently operating coal plants, most of which are aging subcritical plants, are slated to be retired over 2014-2040. Yet, the report also predicts that for each coal plant retired, the world will add about two more coal plants that will feature advanced Clean Coal technologies with carbon capture[2].

To address the growing concerns regarding greenhouse gas and heavy metal emissions and the effects of such greenhouse gas emissions on climate change, many jurisdictions around the world have begun implementing emission standards for their domestic energy producers to meet. For example, the 1990 Clean Air Act Amendments in the United States of America provide the legal guidance on the issue of air pollution control in the United States. In an effort to meet, and in some cases even exceed, such legislated emission standards, energy producers and researchers have focused at least some of their research efforts on identifying systems, techniques, and methods for removing greenhouse gases and other pollutants from emission streams (e.g. flue gas) before such polluting emissions are released into the atmosphere.

Greenhouse gases are atmospheric gases that absorb and emit infrared radiation. $SO_x$ and $NO_x$ species are examples of greenhouse gases and are produced in large quantities from the burning of fossil fuels; they are also major contributors to "acid rain". Owing to their identified detrimental effects on the environment, industry standards now mandate that emission streams must be adequately removed of $SO_x$ and $NO_x$ species prior to release into the environment (including the atmosphere).

Sulfur dioxide (an example of a $SO_x$ species) has traditionally been removed from flue gas through conventional limestone scrubbers utilizing the following underlying chemistry:

$$SO_2 + CaCO_3 \rightarrow CaSO_3 + CO_2 \qquad 1.$$

Conventional limestone scrubbers such as, but not limited to, FGD scrubbers generally have an $SO_2$ capture efficiency of about 90%. This efficiency may be improved to about 95% with the aid of additives. The remaining about 5+% of $SO_2$ that is not captured by conventional limestone scrubbers may be released into the atmosphere and may lead to the formation of health hazardous particulate matter (e.g. condensable PM, PM2.5, PM10) downwind of the flue gas emission. In 2008, the Environmental Protection Agency of the United States of America issued a report showing that 211 counties distributed across 25 states in the United States of America failed to meet federal standards on fine-particle pollution[3]. Despite advances made in $SO_x$ removal from emission streams, the residual amount of $SO_x$ species that is released into the atmosphere still adversely impacts the environment.

In addition, the foregoing chemical reaction of sulfur dioxide and calcium carbonate produces carbon dioxide gas (i.e. a primary greenhouse gas) as a by-product which may be emitted into the atmosphere as a part of the flue gas emissions. For every ton of $SO_2$ captured by a limestone scrubber, about a ton of $CO_2$ is created. Limestone scrubbers also require large volumes of water to create a slurry to "scrub" $SO_x$ species from flue gas, and therefore may operate at less than optimal efficiency in treatment plants situated in locations that experience or are prone to drought or drought-like conditions.

In an effort to decrease $SO_x$ emissions, some energy producers have implemented "fuel-switching" programs, wherein high-sulfur coal is substituted by (or switched with) low-sulfur coal. However, such "fuel-switching" often requires changes to different parts of the energy producing facility in order to accommodate the new fuel. Such changes may include, but are not limited to, changes to boiler design and operating parameters or changes to coal grinding and handling techniques and methods. In addition, because low-sulfur coal has a lower BTU factor than high-sulfur coal, more low-sulfur coal would have to be consumed in order to produce the same level of energy that would otherwise be consumed by consuming high-sulfur coal. Such increased consumption of low-sulfur coal products increases the release of carbon dioxide gas and other pollutants into the atmosphere. In a non-limiting and illustrative example, a 500 MW coal-fired plant may have the following pollutant outputs (see Table 2 below) when fuel in the form of high-sulfur coal or in the form of low-sulfur coal is consumed:

TABLE 2

|  | High Sulfur Coal | Low Sulfur Coal |
| --- | --- | --- |
| $SO_2$ output | about 302 tons/day | about 61 tons/day |
| $NO_x$ output | about 36 tons/day | about 69 tons/day |
| $CO_2$ output | about 10,850 tons/day | about 21,250 tons/day |

$NO_x$ products in flue gas have traditionally been removed by conventional technologies including, but not limited to, boiler modifications and low-$NO_x$ burners. However, industrial players are finding that conventional technologies do not have the ability to meet the increasingly stringent regulatory requirements regarding $NO_x$ removal from flue gas. As such, some industrial players are turning to other technologies. For example, selective catalytic reduction (SCR) has been used to remove $NO_x$ products from flue gas at an efficiency of about 90%. However, SCR processes require high temperatures and the injection of a reagent (e.g. ammonia) over a catalyst. Such a chemical environment may lead to undesirable events such as, but not limited to, catalyst poisoning or ammonia slip.

Nitric oxide (NO) is an example of a $NO_x$ species. The reaction of NO in the gas phase with chlorine gas, bromine gas, or oxygen gas have been previously examined, and reported as being very slow, taking minutes to hours to equilibrate. On the other hand, oxidation of NO to nitrogen dioxide may occur rapidly in the presence of the appropriate species. For example, NO gas may be oxidized rapidly according to reactions 1, 2, and 3 below:

$$NO+O_3 \rightarrow NO_2+O_2; \qquad 2.$$

$$NO+ClO_2 \rightarrow NO_2+ClO; \qquad 3.$$

and $$NO+HNO_3 \rightarrow NO_2+HNO_2. \qquad 4.$$

Referring to reaction 2, NO has been shown to react completely with ozone in 0.6 seconds at 127° C.[4]. Referring to reaction 3, and without being bound by theory, it is believed that the high endothermicity and instability of $ClO_2$ leads to the ready transfer of an oxygen atom to a molecule of NO. Referring to reaction 4, the reaction with $HNO_3$ has been used for NO removal from flue gas using HNO3 vapour in the presence of chlorine gas, with 90% efficiency.

Heavy metal (e.g. mercury) removal from emission streams are conventionally done through activated carbon filter units. However, the activated carbon filter unit is an additional unit that would have to be incorporated into the flue gas treatment system and process design. In addition, heavy metals may also be inadvertently trapped in conventional limestone scrubbers, thereby contaminating the scrubbers and any downstream products (e.g. sludge or gypsum) derived therefrom. It would be desirable to remove heavy metals like mercury within the same processes that remove $SO_x$ and/or $NO_x$ species, and to capture heavy metals with efficiency and low operating costs.

Examples of systems and methods for removing $SO_x$ species, $NO_x$ species, and heavy metals (e.g. mercury) from emission streams that are known in the art include, but are not limited to, examples provided in PCT App. No. PCT/CA1999/000403 and U.S. Pat. No. 4,619,608.

For example, mercury may be removed using a process that includes: scrubbing an oxidized flue gas stream (e.g. oxidized with chlorine gas) with water, or a water solution, of pH less than or equal to 7; and adding sufficient alkali metal halogen salt (e.g. alkali potassium iodide and the like) to precipitate mercury compounds (e.g. as mercuric iodide and the like) from the water or water solution of pH less than or equal to 7.

Four major gases contribute to the greenhouse effect in the troposphere:

TABLE 3

| Greenhouse Gas | Percentage Contribution |
| --- | --- |
| Water Vapour | About 36-70% (depending on season) |
| Carbon dioxide gas | About 9-26% |
| Methane gas | About 4-9% |
| Ozone | About 3-7% |

Water vapour has been identified as the most abundant greenhouse gas in the atmosphere, and yet is fairly poorly measured and understood[5]. Increases in atmospheric temperatures lead to increases in water evaporated from ground storage locations including, but not limited to, rivers, lakes, oceans, reservoirs, and soil. Warmer air temperatures also lead to higher absolute humidity (i.e. the warmer air has a greater capacity to "hold" more water than cooler air), thereby increasing the water content in the atmosphere. As a greenhouse gas, higher concentrations of water vapour means that more infrared energy radiating from the Earth is absorbed and trapped in the atmosphere, thus further warming the atmosphere. It is desirable to remove water vapour from flue gas and to reuse or recycle the collected water vapour for other applications.

Flue gas generally contains a high water content. For example, the water content in flue gas generated from the combustion of high sulfur coal at a 500 MW coal-fired plant may be about 264,500 lb/hr, or about 8.8% by weight of the flue gas. By comparison, the water content in flue gas generated from the combustion of low sulfur coal at a 500 MW coal-fired plant may be about 1,106,390 lb/hr, or about 10.3% by weight of the flue gas. It is desirable to capture all or at least a portion of the water content in flue gas prior to emission.

Carbon dioxide is a greenhouse gas that is stable and does not burn or react readily with other compounds. Though essential for maintaining life on Earth, carbon dioxide is now concentrated in the Earth's atmosphere at unprecedented levels owing at least in part to anthropogenic emission sources such as, but not limited to, transportation, industrialization, fossil-fuel power production, deforestation, and plant destruction. Due to the growing concerns about climate change, carbon dioxide emissions have come under greater scrutiny by academic, industrial, and governmental players alike.

According to the EIA, in the United States alone, power generation is responsible for over 40% of the country's total $CO_2$ emissions. In 2008, that percentage of total $CO_2$ emission output amounted to about 2.5 billion metric tons. This number is continually growing[6].

Carbon dioxide gas may be converted into commercial products or removed from flue gas. For example, absorption and stripping processes involving aqueous solvents such as amines have been shown to remove carbon dioxide from emission streams such as, but not limited to, flue gas (see for example U.S. Pat. Nos. 4,477,419, 4,152,217, and 7,056,482). Carbon dioxide may also be removed by sodium and calcium based processes (see for example, U.S. application Ser. No. 14/516,284, U.S. Pub. No. 2015/0231562, U.S. application Ser. No. 14/491,015, U.S. Pub. No. 2013/0078159, and U.S. application Ser. No. 14/383,320); however such designs likely add to the overall operating costs of an energy producing facility, if adopted. Carbon dioxide may also be converted to methane through hydrogenation (see for example, U.S. application Ser. No. 14/302,594, U.S. Pat. Nos. 9,353,323, 9,267,211, 9,133,076, 9,090,978, U.S. application Ser. 14/748,686, U.S. Pat. No. 8,754,269, and U.S. application Ser. No. 11/725,716). Carbon dioxide may also be removed from flue gas by burning an electropositive metal in the presence of carbon dioxide to reduce the carbon dioxide to carbon monoxide or elemental carbon (see for example U.S. Pat. No. 9,285,116). Carbon dioxide may also be removed from flue gas by cooling the flue gas by direct contact with a quench liquid (see for example U.S. application Ser. No. 13/100,135). Mixed salt compositions may also be used as carbon dioxide sorbents for carbon dioxide removal from flue gas (see for example U.S. application Ser. Nos. 14/15,283, 13/739,456, 13/869,405, and U.S. Pat. No. 9,101,876). Rare alkali earth metals may also be used for $CO_2$ capture processes such as carbonation of absorption processes; however, such processes are generally complicated, rely on chlor-alkali processes, and increase the operating costs of an energy producing facility. Carbon dioxide may also be removed by reaction with a suitable alkaline earth metal halide (e.g. $MgCl_2$ or $CaCl_2$) or suitable alkaline earth metal hydroxide halide (e.g. Mg(OH)Cl); however such processes require the addition of silicate minerals (e.g. calcium silicate, iron silicate, manganese silicate) as a separate step. The foregoing carbon dioxide conversion or removal processes require a carbon dioxide reactant that consists essentially of carbon dioxide. Pre-treatment of a carbon dioxide containing source (e.g. flue gas), and removing interfering species (e.g. $SO_x$, $NO_x$) therefrom, would be required.

Carbon dioxide gas may be converted into methane gas by the Sabatier process. The Sabatier process involves the hydrogenation of $CO_2$ in the presence of a catalyst (e.g. a nickel catalyst, ruthenium, or alumina) to produce methane, water, and energy. The reaction can be summarized as follows[7]:

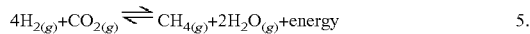

5.

The produced methane from the Sabatier reaction may then be used as a source of fuel in downstream applications. The Sabatier reaction is recognized as a potential means of removing and utilizing carbon dioxide emissions from fossil fuel combustion. However, in order for the Sabatier process to be economically viable as an industrial method of removing and utilizing carbon dioxide emissions from fossil fuel combustion, large amounts of hydrogen gas would need to be produced and/or be available at relatively low cost. To date, the Sabatier reaction has not seen widespread application in industrial settings owing to these requirements/limitations.

Conversion of carbon dioxide into a useful hydrocarbon fuel (e.g. methane) may be desirable. Methane is important for electrical generation, and may be used as a fuel in gas turbines or steam generators. Compared to other hydrocarbon fuels, methane produces less carbon dioxide for each unit of heat released. For example, at about 891 kJ/mol, methane's heat of combustion is lower than any other hydrocarbon but the ratio of the heat combustion (891 kJ/mol) to the molecular mass (16.0 g/mol of which 12.0 g/mol is carbon) shows that methane, being the simplest hydrocarbon, produces more heat per mass unit (55.7 kJ/mol) than other complex hydrocarbons. Methane may be used in various chemical processes, or as a fuel for homes and automobiles in the form of compressed natural gas which may be more environmentally friendly than other fuel sources like gasoline/petrol and diesel.

Liquefied Natural Gas (LNG) is predominantly methane that has been converted to liquid form for ease of storage or transport. The methane is condensed into a liquid at about atmospheric pressure. LNG takes up about 1/600 the volume of natural gas in the gaseous state. It is odorless, colorless, non-toxic and non-corrosive. LNG achieves a higher reduction in volume than compressed natural gas (CNG). The energy density of LNG may be 2.4 times greater than that of CNG or may be about 60% that of diesel fuel. LNG is generally cost efficient to transport over long distances where pipelines do not exist. Specifically designed cryogenic sea vessels (LNG carriers) or cryogenic road tankers may be used for LNG transport.

No admission is necessarily intended, nor should it be construed, that any of the preceding information constitutes prior art against the present invention.

SUMMARY

Various embodiments of this disclosure relate to a system comprising: (a) a reactor configured to receive a gas stream comprising $NO_x$ species and carbon dioxide gas, the reactor further configured to oxidize the $NO_x$ species in the gas stream to produce hydrochloric acid; (b) an electrolytic unit configured to receive the hydrochloric acid and configured to electrolyse the hydrochloric acid to produce hydrogen gas; and (c) a carbon dioxide absorber (e.g. a "Sabatier reactor") configured to receive the gas stream from the reactor and the hydrogen gas from the electrolytic unit, the hydrogen gas for hydrogenating the carbon dioxide gas in the gas stream into a hydrocarbon fuel.

The carbon dioxide gas may be converted to the hydrocarbon fuel by the Sabatier reaction.

The Sabatier reaction may use a catalyst selected from the group consisting of a nickel catalyst, a ruthenium catalyst, an alumina catalyst, and a copper catalyst.

Various embodiments of this disclosure relate to a system comprising: (a) a gas phase reactor configured to receive a gas stream comprising $NO_x$ species, water vapour, and carbon dioxide gas, the gas phase reactor further configured to oxidize the $NO_x$ species in the gas stream to produce hydrochloric acid; (b) a $NO_x$ absorber configured to receive the gas stream from the gas phase reactor, the $NO_x$ absorber further configured to oxidize the $NO_x$ species in the gas stream, the $NO_x$ absorber further configured to collect the hydrochloric acid produced from oxidizing the $NO_x$ species in the gas stream in the $NO_x$ absorber and oxidizing the $NO_x$ species in the gas phase reactor; (c) an electrolytic unit configure to receive the hydrochloric acid collected at the $NO_x$ absorber, and further configured to electrolyse the hydrochloric acid to produce hydrogen gas; (d) a water vapour remover configured to receive the gas stream from the $NO_x$ absorber, and further configured to remove the water vapour from the gas stream; and (e) a carbon dioxide absorber configured to receive the gas stream from the water vapour removal apparatus and the hydrogen gas from the electrolytic unit, the hydrogen gas for hydrogenating the carbon dioxide gas in the gas stream into a hydrocarbon fuel.

Various embodiments of this disclosure relate to a method of treating a gas stream comprising $NO_x$ species, water vapour, and carbon dioxide gas, the method comprising: (a)

generating hydroxyl radicals and chlorine radicals; (b) oxidizing the NO$_x$ species in the gas stream with the hydroxyl radicals and chlorine radicals to produce nitric acid and hydrochloric acid; (c) removing the water vapour from the gas stream; (d) reacting the carbon dioxide gas with hydrogen gas produced from electrolyzing the water vapour removed from the gas stream, the hydrochloric acid, or both, to produce a hydrocarbon fuel.

Various embodiments of this disclosure relate to a system comprising: (a) a gas phase oxidation (GPO) reactor configured to receive a flue gas stream comprising NOx species and carbon dioxide gas, the GPO reactor further configured to receive chlorine gas, liquid or solution, and to oxidize the NOx species in the flue gas stream to produce a gas stream comprising nitric acid and hydrochloric acid; (b) an electrolytic unit configured to receive the hydrochloric acid and configured to electrolyse the hydrochloric acid to produce hydrogen gas and chlorine gas; and (c) a Sabatier reactor configured to receive both a gas stream, downstream from the GPO reactor, and at least a portion of the hydrogen gas from the electrolytic unit, the Sabatier reactor further configured to hydrogenate the carbon dioxide gas in the gas stream into a hydrocarbon fuel comprising methane.

Various embodiments of this disclosure relate to a method of producing a hydrocarbon fuel, comprising methane, from a flue gas stream comprising NOx species, water vapour, and carbon dioxide gas, the method comprising: (a) generating hydroxyl radicals and chlorine radicals; (b) oxidizing the NOx species in the gas stream with the hydroxyl radicals and chlorine radicals to produce a gas stream comprising nitric acid and hydrochloric acid, water vapour and carbon dioxide gas; (c) removing the water vapour from the gas stream to produce a dehydrated gas stream; (d) producing hydrogen gas from one or both of: (di) electrolyzing the water vapour removed from the gas stream in (c); and (dii) electrolyzing the hydrochloric acid produced in (b); (e) using a Sabatier reaction to hydrogenate the carbon dioxide gas in the dehydrated gas stream from (c) with the hydrogen gas produced in (d) to produce the hydrocarbon fuel.

According to another aspect of the disclosure, there is a use of the Sabatier reaction for converting carbon dioxide gas into a hydrocarbon fuel in an industrial-size flue gas treatment system.

This summary does not necessarily describe the entire scope of all aspects of the disclosure. Other aspects, features and advantages will be apparent to those of ordinary skill in the art upon review of the following description of specific embodiments.

BRIEF DESCRIPTION OF THE DRAWINGS

In the accompanying drawings, which illustrate one or more exemplary embodiments.

DETAILED DESCRIPTION

Figure 1:
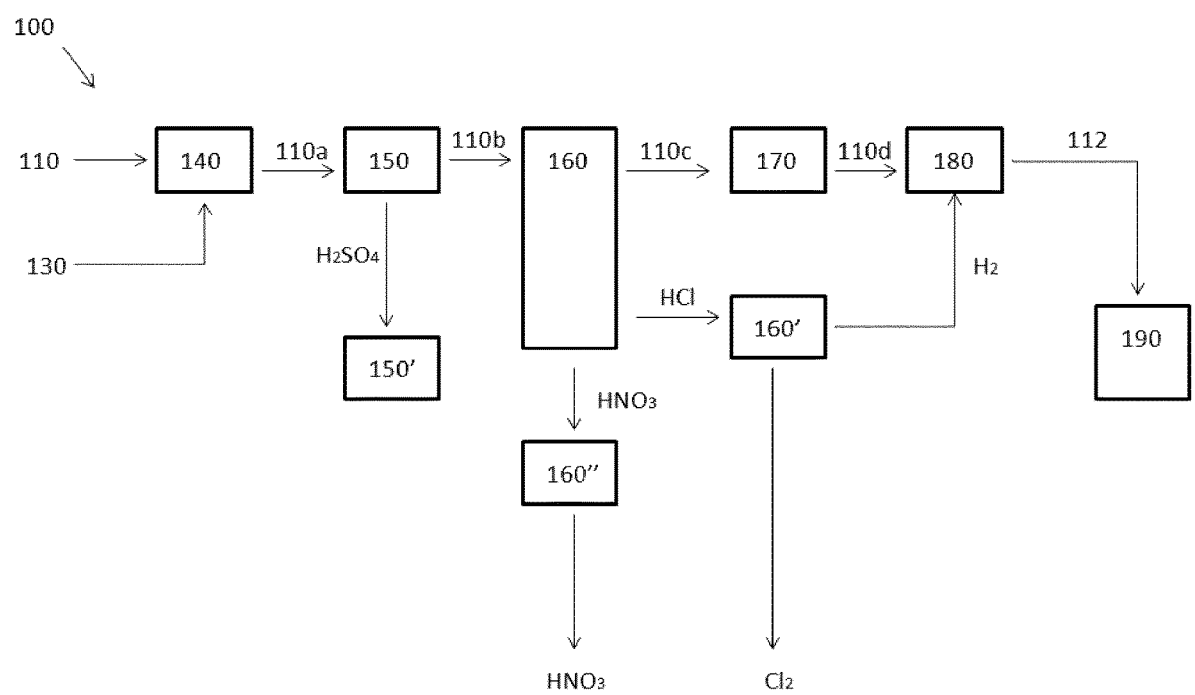
FIG. 1 is a flue gas treatment system for use in a coal-firing facility according to an embodiment, the treatment system comprising a gas phase reactor, a SO$_x$ absorber, a NO$_x$ absorber, a water vapour remover, and a carbon dioxide absorber.

Directional terms such as "top", "bottom", "upwards", "downwards", "vertically", and "laterally" are used in the following description for the purpose of providing relative reference only, and are not intended to suggest any limitations on how any article is to be positioned during use, or to be mounted in an assembly or relative to an environment.

Any element expressed in the singular form also encompasses its plural form. Any element expressed in the plural form also encompasses its singular form. The use of the word "a" or "an" when used herein in conjunction with the term "comprising" may mean "one", but it is also consistent with the meaning of "one or more", "at least one", and "one or more than one".

As used herein, the terms "comprising", "having", "including", and "containing", and grammatical variations thereof, are inclusive or open-ended and do not exclude additional, un-recited elements and/or method steps. The term "consisting essentially of" when used herein in connection with a composition, use or method, denotes that additional elements, method steps or both additional elements and method steps may be present, but that these additions do not materially affect the manner in which the recited composition, method or use functions. The term "consisting of" when used herein in connection with a composition, use or method, excludes the presence of additional elements and/or method steps.

As used herein, the term "about" when followed by a recited value means plus or minus 10% of the recited value.

The present disclosure relates to a system and a method for removing greenhouse gases and other pollutants from an emission stream (e.g. flue gas). Greenhouse gases and other pollutants may include, without limitation, one or more of: SO$_x$ (e.g. SO$_2$), NO$_x$ (e.g. NO, NO$_2$), H$_2$S, water vapour, carbon dioxide, heavy metals (e.g. mercury), soot, smoke, dust, and trace elements.

The present disclosure also relates to systems and methods for removing water vapour and carbon dioxide gas from the emission stream (e.g. flue gas), and for converting the carbon dioxide gas into a hydrocarbon fuel via the Sabatier process. It is contemplated that the system may be able to internally produce a large enough volume of hydrogen gas to drive the Sabatier process and remove carbon dioxide gas from the emission stream. It is also contemplated that the Sabatier process may be incorporated into an industrial scale setting and be economically competitive against conventional emission stream treatment methods.

Emission streams may be pre-cleaned through an electrostatic precipitator (an "ESP"), as known in the art, to remove fine particles such as, but not limited to, dust, soot, smoke, and trace elements. Trace elements include, but are not limited to, antimony, arsenic, cadmium, chromium, nickel, selenium, and zirconium, all of which have been identified as elements that have detrimental impacts on the environment and human health. However, even if the ESP operates at about 99% efficiency, a portion of these trace elements pass through the ESP. The remaining trace elements are captured in sulfuric acid produced by the oxidation of SO$_x$ species (described below) where they may be removed by ion exchange.

NO$_x$ species in the emission stream may be oxidized to produce hydrochloric acid and nitric acid. The produced nitric acid may be sold as is, and the produced hydrochloric acid may be electrolyzed to produce hydrogen gas and chlorine gas. The hydrogen gas may be used to hydrogenate the carbon dioxide gas present in the flue gas to a hydrocarbon fuel. The chlorine gas may be used to generate chlorine radicals required in the oxidation of SO$_x$ species, NO$_x$ species, and heavy metals (e.g. mercury) present in the emissions stream.

Water vapour in the emission stream may be removed from the emission stream and electrolyzed to form hydrogen gas and oxygen gas. The hydrogen gas may be used to hydrogenate the carbon dioxide gas present in the emission stream to a hydrocarbon fuel. The oxygen gas may be directed to a furnace of the system to aid in combustion or sold.

The hydrocarbon fuel produced from the hydrogenation of carbon dioxide via, for example, the Sabatier process may be condensed further to reduce gas volumes and to aid in storage and transport. In some instances, produced hydrocarbon fuel may be condensed up to about 600%.

Thus, various embodiments of the present disclosure relate to a system, e.g. a flue gas treatment system configured for use with a coal-firing facility or a gas-burning facility. The system includes, at a minimum: (a) a gas phase oxidation (GPO) reactor (referred elsewhere herein as a "gas phase reactor"), (b) an electrolytic unit, and (c) a Sabatier reactor (also referred to herein as a "carbon dioxide absorber"). The flue gas may be from a coal-firing plant or a gas-burning plant, or from any other flue gas source. In some embodiments, the flue gas will have been pre-cleaned as described above (e.g. through an ESP). The flue gas comprises $NO_x$ species (e.g. NO, $NO_2$), and carbon dioxide gas and may further comprise one or more of: water vapour, $SO_x$ species (e.g. $SO_2$), mercury and/or heavy metal trace elements. In some embodiments, the flue gas comprises SOx species, $NO_x$ species, water vapour, mercury, carbon dioxide gas and may further comprise heavy metal trace elements.

In some embodiments, the system further includes water vapour remover. In some embodiments, the system further includes a $NO_x$ absorber. In some embodiments, the system further includes a SOx absorber. In some embodiments, the system includes: a GPO reactor, a SOx absorber, a $NO_x$ absorber, an electrolytic unit, a water vapour remover and a Sabatier reactor. Primary products of these systems are nitric acid and methane, the latter of which may be used on site, stored compressed or converted to liquefied natural gas (LNG). For any of the above embodiments, the system may thus further comprise a compressor for compressing the methane or a condenser for condensing the methane into LNG. Depending on the components of the flue gas, other products of these systems may include sulfuric acid and/or mercury. HCl and $H_2(g)$ are also produced, and in certain embodiments may be recycled into the system. $O_2$ (g) may also be produced, and in certain embodiments may be recycled into the system.

The GPO reactor is configured to receive a flue gas stream, and is further configured for oxidation of the $NO_x$ species in the flue gas. In some embodiments, for example, the GPO reactor is configured to further receive chlorine (as gas, a liquid or in solution), which oxidizes the $NO_x$ species in the flue gas to produce a gas stream (i.e. a product gas stream) which comprises, among other things, nitric acid and hydrochloric acid.

In some embodiments, the chlorine is a chlorine gas and the GPO reactor is configured to receive a chlorine gas stream. In such embodiments, chlorine gas and flue gas may be: (i) delivered into the GPO reactor operating at pre-set reaction conditions; and (ii) mixed in the GPO reactor. The GPO reactor may be a reactor that is known in the art, such as a commercially available gas phase reactor that can adequately mix the gases. Appropriate reaction conditions are also known in the art (see for example U.S. Pat. No. 4,619,608). For example, the GPO reactor may be set at a temperature between about 100° C. and about 650° C. For example, the temperature of the GPO reactor may be set at about 100° C., 125° C., 150° C., 175° C., 200° C., 225° C., 250° C., 275° C., 300° C., 325° C., 350° C., 375° C., 400° C., 425° C., 450° C., 475° C., 500° C., 525° C., 550° C., 575° C., 600° C., 625° C., 650° C., or any temperature therebetween.

At elevated temperatures in the GPO reactor, it is believed that chlorine gas reacts with water vapour in the flue gas to generate chlorine radicals and hydroxyl radicals. The $NO_x$ species or a portion thereof present in the flue gas is oxidized in the GPO reactor in the presence of the generated chlorine radicals and the generated hydroxyl radicals. Using nitric oxide (NO) as an non-limiting example of a $NO_x$ species, and without wishing to be bound by theory, it is believed that nitric oxide (NO) in flue gas is oxidized to nitric acid ($HNO_3$) and hydrochloric acid in the GPO reactor according to the following chemical reactions:

$$NO + \cdot OH \rightarrow HNO_2; \qquad 6.$$

$$NO + \cdot Cl \rightarrow NOCl; \qquad 7.$$

$$NOCl + H_2O \rightarrow HNO_2 + HCl; \qquad 8.$$

$$HNO_2 + \cdot Cl \rightarrow NO_2 + HCl; \qquad 9.$$

$$NO_2 + \cdot OH \rightarrow HNO_3; \qquad 10.$$

$$NO_2 + \cdot Cl \rightarrow NO_2Cl; \qquad 11.$$

$$NO_2Cl + H_2O \rightarrow HNO_3 + HCl. \qquad 12.$$

Without being bound by theory, it is also believed that the oxidized forms of polluting species are more readily removable from flue gas than the non-oxidized forms thereof. In addition, it is believed that the predominant final products of $NO_x$ removal are nitric acid and hydrochloric acid. The gas stream exiting the GPO reactor (i.e. the product gas stream) thus comprises dissolved nitric acid and hydrochloric acid and other pollutants (e.g. $CO_2$ (g), and in some cases one or more of water vapour, sulfuric acid, $HgCl_2$, trace heavy metals, and may further include remaining non-oxidized $NO_x$ species, $SO_x$ species, and/or non-chlorinated mercury.

The product gas stream may be substantially free of $NO_x$ species or may benefit from further oxidation to yield a product gas stream that is substantially free of $NO_x$ species. When present in the flue gas, SOx species will also be oxidized in the GPO reactor, forming sulfuric acid. In such case, the product gas stream may be substantially free of $SO_x$ species or may benefit from further oxidation to yield a product gas stream that is substantially free of $SO_x$ species.

For example, in some embodiments (e.g. when the flue gas comprises $SO_x$ species), the system may further comprise a $SO_x$ absorber configured to receive the product gas stream from the GPO reactor or a further processed gas stream, downstream from the GPO reactor. Such systems may further include a $NO_x$ absorber. For example, the $SO_x$ absorber may be positioned in series between the $NO_x$ absorber and the GPO reactor. In some embodiments, the system further includes a $SO_x$ absorber and does not include a $NO_x$ absorber. For example, the $SO_x$ absorber may be positioned in series between the GPO reactor and the Sabatier reactor, or between the GPO reactor and a water vapour remover.

In embodiments that further comprise a $SO_x$ absorber, $SO_x$ absorber may be configured to receive the product gas stream from the GPO reactor or a further processed gas stream, downstream from GPO reactor, and may be further configured to collect from the gas stream the oxidized $SO_x$ species converted in the GPO reactor.

The $SO_x$ absorber may be any suitable absorber that is known in the art. For example, the $SO_x$ absorber may be one that is substantially similar to the one described in U.S. Pat. No. 4,619,608 both in design and reaction conditions. The $SO_x$ absorber may achieve $SO_2$ capture rates of above 99% without producing $CO_2$ as a by-product. Where $CO_2$ capture and storage by sequestration is desired, $SO_x$ limits of 10 ppm or below may be required. Conventional limestone scrubbers may not remove $SO_2$ from flue gas with the same efficiency.

The $SO_x$ absorber may be arranged horizontally or vertically, depending on spatial restrictions or requirements of the system. The $SO_x$ absorber may also comprise packed towers or cross-flow vessels that condense and collect one or more resulting acid streams, e.g. one or more of sulfuric acid, nitric acid, hydrochloric acid, and/or other acid streams, and may further collect as mercury products and/or trace heavy metal products. The $SO_x$ absorber may be a single integrated absorber or consist of a plurality of non-integrated components. The $SO_x$ absorber may be a single $SO_x$ absorber unit, or may comprise a plurality of $SO_x$ absorber units.

In addition to oxidizing $NO_x$ species, the conditions in the GPO reactor also oxidize SOx species. In the $SO_x$ absorber, additional solution chemistry may occur to aid in oxidation and/or collection and to build up the strengths of the acids. For example, but without limitation, water may circulated in the $SO_x$ absorber or steam may be sprayed into the $SO_x$ absorber. This oxidation process converts $SO_x$ species to sulfuric acid so as to convert the remaining $SO_x$ species to sulfuric acid. In the presence of steam, $SO_x$ generally reacts in preferential order over $NO_x$. Using sulfur dioxide ($SO_2$) as a non-limiting example of a $SO_x$ species, and without wishing to be bound by theory, it is believed that the sulfur dioxide is oxidized to sulfuric acid ($H_2SO_4$) in the $SO_x$ absorber according to the following chemical reaction:

$$SO_2 + Cl_2 + 2H_2O \rightarrow H_2SO_4 + 2HCl \qquad 13.$$

$SO_2$ removal rates of about 99% may be achieved at $Cl_2$ levels as low as 1.0 $Cl_2/SO_2$ molar ratio. An equilibrium concentration of about 70% or higher $H_2SO_4$ to $H_2O$ may also be achieved. The collected mixture of $H_2SO_4/H_2O$ may be further treated by a process to remove $H_2O$, thereby concentrating the remaining sulfuric acid to a purity of up to about 93-96% (commercial grade). The purified $H_2SO_4$ may then be collected and shipped to industry for sale. Accordingly, in certain embodiments, the system may further comprise means for removing water from the mixture of $H_2SO_4/H_2O$.

In some embodiments (e.g. when the flue gas further comprises mercury), the $SO_x$ absorber may be further configured to remove the mercury. For example, but without limitation, the $HgCl_2$ produced by halogenation reaction in the GPO reactor, and/or produced in the $SO_x$ absorber itself, may be captured in the condensed sulfuric acid that is collected by the $SO_x$ absorber. The $SO_x$ absorber may be further configured to convert metallic mercury remaining in the gas stream to $HgCl_2$ and to collect the produced $HgCl_2$. Mercuric halides (e.g. mercuric chloride) in the sulfuric acid (wherever produced) may be separated out using various methods, e.g. but not limited to, any described in PCT/CA1999/000403. In one non-limiting example, an alkali metal halogen (e.g. potassium iodide) salt is added to precipitate mercuric iodide (see PCT/CA1999/000403). In other embodiments, the system may not be configured for heavy metal removal. Yet in other embodiments, mercury recovery from the collected sulfuric acid may occur at an off-site location.

In some embodiments (e.g. when the flue gas further comprises at least one heavy metal trace element), the $SO_x$ absorber or the system may be further configured to remove the at least one heavy metal trace element (e.g. one or more of antimony, arsenic, cadmium, chromium, nickel, selenium, and zirconium). For example, but without limitation, the trace elements may be captured in the sulfuric acid produced from oxidizing the $SO_x$ species and condensed in the $SO_x$ absorber. In some embodiments, the system further comprises means for removing the trace elements from the sulfuric acid by ion exchange. In other embodiments, trace element removal may not occur. Yet in other embodiments, trace element removal may occur at an off-site location.

As discussed, in some embodiments the system may further comprise a $NO_x$ absorber configured to receive the product gas stream from the GPO reactor or a further processed gas stream, downstream from the GPO reactor (e.g. a gas stream exiting a $SO_x$ absorber). As discussed, such systems may further include a $SO_x$ absorber. For example, the $NO_x$ absorber may be positioned in series between the $SO_x$ absorber and the Sabatier reactor, or between the $SO_x$ absorber and a water vapour remover. In some embodiments, the system further includes a $NO_x$ absorber and does not include a $SO_x$ absorber. For example, the $NO_x$ absorber may be positioned in series between the GPO reactor and the Sabatier reactor, or between the GPO reactor and a water vapour remover.

The $NO_x$ absorber is further configured to collect oxidized $NO_x$ species converted in the GPO reactor. The $NO_x$ absorber may be any absorber that is known in the art to be suitable for this purpose. For example, the $NO_x$ absorber may be one that is substantially similar to the one described in U.S. Pat. No. 4,619,608 both in design and reaction conditions. $NO_x$ removal efficiency of about 98% may be achieved by the combination of a GPO reactor and a $NO_x$ absorber. When no ammonia is used in a $NO_x$ absorber, there is no ammonia slip. The $NO_x$ absorber may be arranged horizontally or vertically, depending on spatial restrictions or requirements of the system. The $NO_x$ absorber may also comprise packed towers or cross-flow vessels that condense and collect nitric acid, hydrochloric acid, as well as heavy metal products (e.g. $HgCl_2$). In some embodiments, the $NO_x$ absorber is a plurality of $NO_x$ absorber units. In some embodiments, the $NO_x$ absorber may be a single $NO_x$ absorber unit.

In some embodiments, the NOx absorber may be further configured to further oxidize $NO_x$ species that may remain in the product gas stream (e.g. from the GPO reactor) or in the further treated gas stream (e.g. from the $SO_x$ reactor), so as to convert the remaining $NO_x$ species to nitric acid and hydrochloric acid. For example, the gas stream entering the $NO_x$ absorber may be sprayed with steam to further oxidize the $NO_x$ species. The gas stream may be sprayed with steam at a non-zero angle (e.g. orthogonally). The gas stream may be sprayed with steam at a suitable spraying pressure. Without being bound by theory, it is believed that the following reactions are involved in the removal of $NO_x$ species from gas stream in the $NO_x$ absorber:

$$Cl_2 + H_2O \rightarrow HOCl + HCl \qquad 14.$$

$$NOCl + H_2O \rightarrow HNO_2 + HCl \qquad 15.$$

$$NOCl + HOCl + H_2O \rightarrow HNO_3 + 2HCl \qquad 16.$$

$$NO_2Cl+H_2O \rightarrow HNO_2+HOCl \qquad 17.$$

$$2NO_2+H_2O \rightarrow HNO_2+HNO_3 \qquad 18.$$

$$HNO_2+HOCl \rightarrow HNO_3+HCl \qquad 19.$$

$$2NO+H_2O+HNO_3 \rightarrow 3HNO_2 \qquad 20.$$

It is thus believed that the predominant final products of $NO_x$ removal are nitric acid and hydrochloric acid.

The $NO_x$ absorber may collect nitric acid having a purity of up to about 99% that may be directed to further processing and/or storage in preparation for commercial shipment and/or sale.

In certain embodiments, the $NO_x$ absorber is configured to remove mercury and/or heavy metal trace elements, using equipment and process(es) known in the art, e.g. but not limited to those described in PCT/CA1999/000403 or described elsewhere herein.

In some embodiments, the $NO_x$ absorber may be configured to collect the hydrochloric acid and to direct at least a portion of the hydrochloric acid from the $NO_x$ absorber to the electrolytic unit. At the electrolytic unit, the HCl undergoes electrolysis to produce hydrogen gas and chlorine gas. Methods of electrolysing hydrochloric acid are known in the art, and any suitable commercially available electrolytic unit may be used. In a non-limiting example, the electrolytic unit comprises high temperature electrolysis cells. The electrolytic unit is thus configured to receive the hydrochloric acid (e.g. from the $NO_x$ absorber, or a portion of which is from the $NO_x$ absorber) and is further configured to electrolyse the hydrochloric acid to produce both hydrogen gas and chlorine gas. In alternative embodiments, the system may be configured to direct HCl separated from the condensed products of the $SO_x$ absorber to the electrolytic unit.

The hydrogen gas produced from the electrolysis of HCl at the electrolytic unit may be re-used in the system or elsewhere in the plant, or potentially stored, e.g. for sale/transport. In a non-limiting example, the produced hydrogen gas or a portion thereof is re-directed to the Sabatier reactor for use in converting carbon dioxide gas into a hydrocarbon fuel. The chlorine gas produced from the electrolysis of HCl at electrolytic unit (or a portion thereof) may be re-used in the system or elsewhere in the plant, or potentially stored, e.g. for sale/transport. In a non-limiting example, the system is further configured to direct the chlorine gas produced in the electrolytic unit to supply all or a portion of the chlorine gas stream for GPO reactor.

In some embodiments, the system may be configured such that the product gas stream leaving the GPO reactor is fed directly to the Sabatier reactor. In other embodiments, additional components (e.g. $SO_x$ absorber(s), $NO_x$ absorber(s) and/or water vapour remover(s)) to treat the product gas stream are included in series between the GPO reactor and the Sabatier reactor to treat (further process or clean) the gas stream for a more efficient Sabatier reaction.

For example, in some embodiments (e.g. when the flue gas further comprises water vapour), the system further comprises a water vapour remover configured to remove the water vapour from the gas stream before reaching the Sabatier reactor. The water vapour remover may be positioned in series in the system between the $NO_x$ absorber and the Sabatier reactor. The water vapour remover may be positioned in series between the $SO_x$ absorber and the Sabatier reactor. The water vapour remover may be positioned in series between the GPO reactor and the Sabatier reaction, e.g. immediately prior to receiving the treated gas stream at Sabatier reactor. The water vapour remover may be configured in parallel to the electrolytic unit.

Any suitable water vapour remover may be used, as is well known in the art. In a non-limiting example, thermal energy generated from the system itself (e.g. heat from excess steam, or heat added specifically for the step of water vapour removal is used to heat the gas stream to evaporate any $H_2O$ content remaining therein, the evaporated $H_2O$ content being collectable downstream. In another non-limiting example, water vapour is removed from the gas stream by heat exchangers and the removed water vapour may be collected as steam. Without such treatment or removal step, the water vapour generally would otherwise be vented into the atmosphere. The system may be configured to use the collected steam or to condense the steam to liquid water (e.g. by cooling). Accordingly, in certain embodiments, the system may be further configured to recycle the collected water content (steam or liquid water) back into the system. For example, but without limitation, the system may be configured to: (i) return the $H_2O$ content to a steam cycle of the system; (ii) re-use the $H_2O$ content recovered from the gas stream as process water in the $SO_x$ absorber (if present), the $NO_x$ absorber (if present), or both the $SO_x$ absorber and the $NO_x$ absorber; (iii) use the $H_2O$ content recovered from the gas stream to aid in the electrolysis of HCl in the electrolytic unit; and/or (iv) use the $H_2O$ content recovered from the gas stream as a heat source to increase the temperature of the electrolytic reaction of HCl in the electrolytic unit, thereby improving the efficiency of electrolysis. Such recycling of evaporated $H_2O$ content from flue gas may be desired, particularly for flue gas treatment systems that are situated in locations that experience or are prone to drought or drought-like conditions. It is estimated that, for a 500 MW plant, up to about 750,000 lbs/hr of $H_2O$ content that would otherwise be vented into the atmosphere as steam may be recovered and re-used within the system herein.

In some embodiments, the system is configured to direct the $H_2O$ content collected in the water vapour remover (or a portion thereof) to a separate water electrolytic unit configure to convert the water to hydrogen gas and oxygen gas. In these embodiments, the system may be configured to direct the hydrogen gas generated from the electrolysis of the collected $H_2O$ content (or a portion thereof) to the Sabatier reactor. The system may be further configured to use the oxygen gas generated from the electrolysis as a fuel source within the system or elsewhere in the plant. In other embodiments, the collected water content removed from the gas stream in the water vapour remover does not undergo further hydrolysis.

The water vapour remover is configured to direct the resulting dehydrated gas stream (comprising $CO_2$ gas or consisting essentially of $CO_2$ gas) to the Sabatier reactor.

The Sabatier reactor is configured to receive a gas stream (i.e. the product gas stream of the GPO reactor or a further treated gas stream downstream from the GPO reactor) and is further configured to receive a hydrogen gas stream (e.g. from one or more electrolytic units electrolyzing HCl and/or water). For example, the Sabatier reactor may be configured to receive a gas stream from the $SO_x$ absorber, the $NO_x$ absorber or the water vapour remover. In certain embodiments, the Sabatier reactor is configured to receive a gas stream from the water vapour remover.

The Sabatier process is catalyzed in the Sabatier reactor by an appropriate catalyst such as, but not limited to, a nickel catalyst, ruthenium, alumina, or a copper catalyst. In certain embodiments, the catalyst is a copper catalyst. In certain embodiments, the Sabatier reactor is configured for the Sabatier reaction to occur at atmospheric pressure. In some embodiments, the molar feed ratio of $H_2:CO_2$ is greater than or equal to about 3.5:1, and the Sabatier process may be carried out at a temperature between about 400° F. and about 700° F. In other embodiments, other suitable reaction parameters may be used. Any suitable Sabatier reactor and conditions may be used.

In the Sabatier reactor, the Sabatier reaction hydrogenates the carbon dioxide gas in the product gas stream into a hydrocarbon fuel. In some embodiments, the hydrocarbon fuel comprises methane. In some embodiments, the hydrocarbon fuel consists essentially of methane.

In some embodiments, the system may be further configured to direct the methane (or a portion thereof) to a boiler or combustion chamber configured to combust the methane to generate heat or power. For example, the methane (or a portion thereof) may be blended and co-fired with coal at the plant, or may be used as a fuel to power a separate turbine. In some embodiments, the system may further comprise a compressor or condenser configured to condense liquefied natural gas from the methane (or a portion thereof). In some embodiments, the system may further comprise a compressor configured to condense the volume of the hydrocarbon fuel, e.g. for transport from the plant.

In other non-limiting examples, the system may be further configured to convert the methane (or a portion thereof) to other products such as, but not limited to, a methyl halide. In a non-limiting example, methane (or a portion thereof) may be converted to chloromethane through the following reaction, as known in the art:

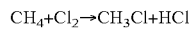

$$CH_4 + Cl_2 \rightarrow CH_3Cl + HCl \qquad 21.$$

The resulting methyl chloride may be further processed into other organic polyhalides, such as dichloro-methane. The resulting methyl chloride may also be converted to other products like methyl alcohols, ethyl alcohols, ethers, aldehydes, ketones, organic acids, esters, amines, and fats and soaps.

In various embodiments, the system may comprise: (a) a GPO reactor configured to receive a gas stream comprising $SO_x$ species, $NO_x$ species, water vapour, heavy metals, and carbon dioxide gas, the GPO reactor further configured to oxidize the $SO_x$ species and $NO_x$ species; (b) a $SO_x$ absorber configured to receive the gas stream from the GPO reactor, the $SO_x$ absorber further configured to further oxidize and collect the $SO_x$ species as $H_2SO_4$; (c) a $NO_x$ absorber configured to receive the gas stream from the $SO_x$ absorber, the $NO_x$ absorber further configured to further oxidize the $NO_x$ species in the gas stream, the $NO_x$ absorber further configured to collect hydrochloric acid produced from oxidizing the $NO_x$ species; (d) an electrolytic unit configured to receive the hydrochloric acid collected at the $NO_x$ absorber, and further configured to electrolyse the hydrochloric acid to produce hydrogen gas; (e) a water vapour remover configured to receive the gas stream from the $NO_x$ absorber, and further configured to remove water vapour from the gas stream; and (f) a Sabatier reactor configured to receive the gas stream from the water vapour remover and the hydrogen gas from the electrolytic unit, the hydrogen gas for hydrogenating the carbon dioxide gas in the gas stream into a hydrocarbon fuel comprising methane.

The present disclosure also relates to a method of producing a hydrocarbon fuel from a flue gas stream comprising $NO_x$ species, water vapour, and carbon dioxide gas. Without limitation, the flue gas may be from a coal-firing facility or a gas-burning facility. As such, the flue gas may further comprise $SO_x$ species, mercury, and/or heavy metal trace elements. In some embodiments, the flue gas will have been pre-cleaned as described above (e.g. through an ESP). In some embodiments, the hydrocarbon fuel comprises methane. In some embodiments, the hydrocarbon fuel consists essentially of methane.

The method comprises: (a) generating hydroxyl radicals and chlorine radicals; (b) oxidizing the $NO_x$ species in the gas stream with the hydroxyl radicals and chlorine radicals to produce a gas stream comprising nitric acid and hydrochloric acid, water vapour and carbon dioxide gas; (c) removing the water vapour from the gas stream to produce a dehydrated gas stream; (d) producing hydrogen gas from one or both of: (di) electrolyzing the water vapour removed from the gas stream in step (c) to produce hydrogen gas and oxygen gas; and (dii) electrolyzing the hydrochloric acid produced in step (b) to produce hydrogen gas and chlorine gas; (e) using a Sabatier reaction to hydrogenate the carbon dioxide gas in the dehydrated gas stream from (c) with the hydrogen gas produced in step (d) to produce the hydrocarbon fuel.

In embodiments where the flue gas stream further comprises $SO_x$ species, the method may further comprise step (bi) oxidizing the $SO_x$ species (e.g. using the hydroxyl radicals and/or chlorine radicals from step (a), and/or by using steam or water) to produce sulfuric acid, and removing the sulfuric acid from the gas stream (e.g. using a $SO_x$ absorber as described for the system above) to produce a gas stream that is substantially free of $SO_x$ species. In embodiments where the flue gas stream further comprises heavy metal trace elements (e.g. but not limited to, one or more selected from a group consisting of antimony, arsenic, cadmium, chromium, nickel, selenium, zirconium, and/or any combination thereof), the method further may further comprise removing the trace elements from the gas stream by capturing the trace elements in the sulfuric acid (as described for the system above). In certain embodiments, but without limitation, the trace elements may be removed from the sulfuric acid by ion exchange. In embodiments where the flue gas stream further comprises mercury, the method may further comprise removing the mercury from the gas stream (as described for the system above). In certain embodiments, removing the mercury comprises converting the mercury to $HgCl_2$ and capturing the $HgCl_2$ in sulfuric acid (e.g. collected in a $SO_x$ absorber). The method may further comprise recovering the mercury from the sulfuric acid (as described for the system above). For example, but without limitation, the mercury may be removed from the sulfuric acid by precipitating out mercury by adding an alkali metal halogen (e.g. potassium iodide to precipitate out mercuric iodide (see PCT/CA1999/000403).

In certain embodiments, the method may further comprise step (bii) further oxidizing the $NO_x$ species with steam or water to produce hydrochloric acid and a gas stream that is substantially free of $NO_x$ species (e.g. by passing the gas stream through a $NO_x$ absorber as described above). In certain embodiments of the method that comprise step (dii), i.e. electrolyzing the hydrochloric acid produced from step (a) and/or step (bii) to produce hydrogen gas and chlorine gas, the method may further comprise using the chlorine gas from step (dii) to generate at least some of the chlorine radicals in step (a). In certain embodiments of the method that comprise step (di), i.e. electrolyzing the water vapour, the method further comprises directing the oxygen gas from step (di) to aid in combustion of a fuel to generate heat or power.

In certain embodiments of the method, the Sabatier reaction is catalysed by a catalyst selected from the group consisting of a nickel catalyst, a ruthenium catalyst, an alumina catalyst, and a copper catalyst. In certain embodiments, the catalyst is a copper catalyst.

In certain embodiments, the method further comprises compressing the methane (or the hydrocarbon fuel) to reduce the volume of the methane (or the hydrocarbon fuel). In certain embodiments, the method further comprises condensing the methane to produce liquefied natural gas. In certain embodiments, the method further comprises combusting the methane (or the hydrocarbon fuel) to generate heat or power. In certain embodiments, the method further comprises blending and co-firing the methane with a fuel (e.g. a fossil or hydrocarbon fuel, such as coal, gas, or any other fuel).

The present disclosure also relates to use of a Sabatier reaction for converting carbon dioxide gas into a hydrocarbon fuel in an industrial-size flue gas treatment system. In certain embodiments, but without limitation, the hydrocarbon fuel is methane. In certain embodiments, the hydrocarbon fuel is compressed to reduce its volume (e.g. to facilitate storage or transport). In certain embodiments, the hydrocarbon fuel is condensed to produce liquefied natural gas. In certain embodiments, the hydrocarbon fuel is blended and co-fired with coal.

The present disclosure also relates, without limitation, to the following enumerated embodiments:

Embodiment(s) 1

A system comprising: (a) a reactor configured to receive a gas stream comprising NOx species and carbon dioxide gas, the reactor further configured to oxidize the NOx species in the gas stream to produce hydrochloric acid; (b) an electrolytic unit configured to receive the hydrochloric acid and configured to electrolyse the hydrochloric acid to produce hydrogen gas; and (c) a carbon dioxide absorber configured to receive the gas stream from the reactor and the hydrogen gas from the electrolytic unit, the hydrogen gas for hydrogenating the carbon dioxide gas in the gas stream into a hydrocarbon fuel.

Embodiment(s) 2

The system according to embodiment(s) 1, wherein the reactor is a gas phase reactor.

Embodiment(s) 3

The system according to embodiment(s) 1 or 2, wherein the reactor is further configured to receive a chlorine gas stream.

Embodiment(s) 4

The system according to any one of embodiment(s) 1 to 3, further comprising a NOx absorber.

Embodiment(s) 5

The system according to embodiment(s) 4, wherein the NOx absorber is configured in series between the reactor and the carbon dioxide collector.

Embodiment(s) 6

The system according to any one of embodiment(s) 1 to 5, further comprising a SOx absorber.

Embodiment(s) 7

The system according to any one of embodiment(s) 1 to 6, the gas stream further comprising water vapour, and the system further comprising a water vapour remover.

Embodiment(s) 8

The system according to embodiment(s) 7, wherein the water vapour remover is configured in series between the NOx absorber and the carbon dioxide collector.

Embodiment(s) 9

The system according to embodiment(s) 8, wherein the water vapour remover is configured in parallel to the electrolytic unit.

Embodiment(s) 10

The system according to any one of embodiment(s) 1 to 9, wherein the carbon dioxide gas is converted to the hydrocarbon fuel by a Sabatier reaction.

Embodiment(s) 11

The system according to embodiment(s) 10, wherein the Sabatier reaction uses a catalyst selected from the group consisting of a nickel catalyst, a ruthenium catalyst, an alumina catalyst, and a copper catalyst.

Embodiment(s) 12

The system according to embodiment(s) 11, wherein the catalyst is the copper catalyst.

Embodiment(s) 13

A system comprising: (a) a gas phase reactor configured to receive a gas stream comprising NOx species, water vapour, and carbon dioxide gas, the gas phase reactor further configured to oxidize the NOx species in the gas stream to produce hydrochloric acid; (b) a NOx absorber configured to receive the gas stream from the gas phase reactor, the NOx absorber further configured to oxidize the NOx species in the gas stream, the NOx absorber further configured to collect the hydrochloric acid produced from oxidizing the NOx species in the gas stream in the NOx absorber and oxidizing the NOx species in the gas phase reactor; (c) an electrolytic unit configure to receive the hydrochloric acid collected at the NOx absorber, and further configured to electrolyse the hydrochloric acid to produce hydrogen gas; (d) a water vapour remover configured to receive the gas stream from the NOx absorber, and further configured to remove the water vapour from the gas stream; and (e) a carbon dioxide absorber configured to receive the gas stream from the water vapour remover and the hydrogen gas from the electrolytic unit, the hydrogen gas for hydrogenating the carbon dioxide gas in the gas stream into a hydrocarbon fuel.

Embodiment(s) 14

The system according to embodiment(s) 13, wherein the reactor is further configured to receive a chlorine gas stream.

Embodiment(s) 15

The system according to embodiment(s) 13 or 14, wherein the electrolytic unit is configured to electrolyse the hydrochloric acid to produce the hydrogen gas and chlorine gas.

Embodiment(s) 16

The system according to embodiment(s) 15, wherein the chlorine gas is recycled into the chlorine gas stream.

Embodiment(s) 17

The system according to any one of embodiment(s) 13 to 16, wherein the carbon dioxide gas is converted to the hydrocarbon fuel by a Sabatier reaction.

Embodiment(s) 18

The system according to embodiment(s) 17, wherein the Sabatier reaction uses a catalyst selected from the group consisting of a nickel catalyst, a ruthenium catalyst, an alumina catalyst, and a copper catalyst.

Embodiment(s) 19

A method of treating a gas stream comprising NOx species, water vapour, and carbon dioxide gas, the method comprising: (a) generating hydroxyl radicals and chlorine radicals; (b) oxidizing the NOx species in the gas stream with the hydroxyl radicals and chlorine radicals to produce nitric acid and hydrochloric acid; (c) removing the water vapour from the gas stream; (d) reacting the carbon dioxide gas with hydrogen gas produced from electrolyzing the water vapour removed from the gas stream, the hydrochloric acid, or both, to produce a hydrocarbon fuel.

Embodiment(s) 20

The method according to embodiment(s) 19, the gas stream further comprising SOx species, the method further comprising oxidizing the SOx species.

Embodiment(s) 21

The method according to embodiment(s) 19 or 20, the gas stream further comprising a heavy metal, the method further comprising removing the heavy metal from the gas stream.

Embodiment(s) 22

The method according to embodiment(s) 21, wherein the heavy metal is mercury.

Embodiment(s) 23

The method according to any one of embodiment(s) 20 to 22, the gas stream further comprising trace elements selected from a group consisting of antimony, arsenic, cadmium, chromium, nickel, selenium, zirconium, and any combination thereof, the method further comprising removing the trace elements from the gas stream.

Embodiment(s) 24

The method according to embodiment(s) 23, further comprising capturing the trace elements in sulfuric acid produced from oxidizing the SOx species, and removing the trace elements from the sulfuric acid by ion exchange.

Embodiment(s) 25

The method according to any one of embodiment(s) 19 to 24, further comprising electrolyzing the hydrochloric acid to produce chlorine gas.

Embodiment(s) 26

The method according to embodiment(s) 25, further comprising using the chlorine gas to generate at least some of the chlorine radicals.

Embodiment(s) 27

The method according to any one of embodiment(s) 19 to 26, further comprising electrolyzing the water vapour removed from the gas stream to produce oxygen gas.

Embodiment(s) 28

The method according to embodiment(s) 27, further comprising using the oxygen gas to aid in combustion.

Embodiment(s) 29

The method according to any one of embodiment(s) 19 to 28, wherein the carbon dioxide gas is converted into the hydrocarbon fuel by a Sabatier reaction.

Embodiment(s) 30

The method according to embodiment(s) 29, wherein the Sabatier reaction is catalysed by a catalyst selected from the group consisting of a nickel catalyst, a ruthenium catalyst, an alumina catalyst, and a copper catalyst.

Embodiment(s) 31

Use of a Sabatier reaction for converting carbon dioxide gas into a hydrocarbon fuel in an industrial-size flue gas treatment system.

Embodiment(s) 32

The use according to embodiment(s) 31, wherein the hydrocarbon fuel is methane.

The present invention will be further illustrated in the following non-limiting examples.

EXAMPLE 1

Referring to FIG. 1, and according to an embodiment of the present disclosure, there is a flue gas treatment system 100 configured for use within a coal-firing facility, the system 100 comprising a gas phase reactor 140, a $SO_x$ absorber 150, a $NO_x$ absorber 160, a water vapour remover 170, and a carbon dioxide absorber 180.

Flue gas 110 comprises $SO_x$ species, $NO_x$ species, water vapour, heavy metals (e.g. mercury), and carbon dioxide gas.

Chlorine gas 130 and flue gas 110 are: (i) delivered into the gas phase reactor 140 operating at pre-set reaction conditions; and (ii) mixed in the gas phase reactor 140. The gas phase reactor may be a reactor that is known in the art, such as a commercially available gas phase reactor. Appropriate reaction conditions are also known in the art (see for example U.S. Pat. No. 4,619,608). For example, the gas phase reactor 140 can be set at a temperature between about 100° C. and about 650° C. For example, the temperature of the gas phase reactor 140 can be set at about 100° C., 125° C., 150° C., 175° C., 200° C., 225° C., 250° C., 275° C., 300° C., 325° C., 350° C., 375° C., 400° C., 425° C., 450° C., 475° C., 500° C., 525° C., 550° C., 575° C., 600° C., 625° C., 650° C., or any temperature therebetween.

At elevated temperatures in the gas phase reactor 140, it is believed that chlorine gas 130 reacts with the water vapour in the flue gas 110 to generate chlorine radicals and hydroxyl radicals. The $NO_x$ species or a portion thereof present in the flue gas 110 is oxidized in the gas phase reactor 140 in the presence of the generated chlorine radicals and the generated hydroxyl radicals. Using nitric oxide (NO) as an example of a $NO_x$ species, and without wishing to be bound by theory, it is believed that nitric oxide (NO) in flue gas 110 is oxidized to nitric acid ($HNO_3$) and hydrochloric acid in the gas phase reactor 140 according to the following chemical reactions:

$$NO + \cdot OH \rightarrow HNO_2; \qquad 6.$$

$$NO + \cdot Cl \rightarrow NOCl; \qquad 7.$$

$$NOCl + H_2O \rightarrow HNO_2 + HCl; \qquad 8.$$

$$HNO_2 + \cdot Cl \rightarrow NO_2 + HCl; \qquad 9.$$

$$NO_2 + \cdot OH \rightarrow HNO_3; \qquad 10.$$

$$NO_2 + \cdot Cl \rightarrow NO_2Cl; \qquad 11.$$

$$NO_2Cl + H_2O \rightarrow HNO_3 + HCl. \qquad 12.$$

Without being bound by theory, it is also believed that the oxidized forms of polluting species are more readily removable from flue gas than the non-oxidized forms thereof. In addition, it is believed that the predominant final products of $NO_x$ removal are nitric acid and hydrochloric acid. Gas stream 110a comprising dissolved nitric acid and hydrochloric acid and other pollutants exits the reactor 140 and is directed towards the $SO_x$ absorber 150.

The $SO_x$ absorber 150 may be any suitable absorber that is known in the art. For example, and as contemplated in this embodiment, the $SO_x$ absorber 150 is one that is substantially similar to the one described in U.S. Pat. No. 4,619,608 both in design and reaction conditions. The $SO_x$ absorber 150 may achieve $SO_2$ capture rates of above 99% without producing $CO_2$ as a by-product. Where $CO_2$ capture and storage by sequestration is desired, $SO_x$ limits of 10 ppm or lower may be required. Conventional limestone scrubbers may not remove $SO_2$ from flue gas with the same efficiency.

The $SO_x$ absorber 150 may be arranged horizontally or vertically, depending on spatial restrictions or requirements of the system 100. The $SO_x$ absorber 150 may also comprise packed towers or cross-flow vessels that condense and collect resulting sulfuric acid, nitric acid, hydrochloric acid, or other acid streams, as well as heavy metal (e.g. mercury) products.

In the $SO_x$ absorber 150, the gas stream 110a is sprayed with steam to facilitate $SO_x$ oxidation; in the presence of the steam, $SO_x$ generally reacts in preferential order over $NO_x$. Using sulfur dioxide ($SO_2$) as a non-limiting example of a $SO_x$ species, and without wishing to be bound by theory, it is believed that the sulfur dioxide is oxidized to sulfuric acid ($H_2SO_4$) in the $SO_x$ absorber 150 according to the following chemical reaction:

$$SO_2 + Cl_2 + 2H_2O \rightarrow H_2SO_4 + 2HCl \qquad 13.$$

$SO_2$ removal rates of about 99% may be achieved at $Cl_2$ levels as low as 1.0 $Cl_2/SO_2$ molar ratio. An equilibrium concentration of about 70% or higher $H_2SO_4$ to $H_2O$ may also be achieved. The collected mixture of $H_2SO_4/H_2O$ may be further treated by a process 150' to remove $H_2O$ therefrom, thereby concentrating the remaining sulfuric acid to a purity of up to about 93-96% (commercial grade). The purified $H_2SO_4$ may then be collected and shipped to industry for sale.

Although not shown in FIG. 1, in certain embodiments the method may further comprise removing the heavy metals (or a portion thereof), e.g. mercury, in the $SO_x$ absorber or in the gas stream exiting the $SO_x$ absorber, e.g. by a process known in the art such as, but not limited to, the one described in PCT/CA1999/000403. For example, mercury may be converted into a mercury halide (e.g. mercury chloride) and collected from the sulfuric acid. In certain embodiments, heavy metal removal may or may further comprise capturing the trace elements (e.g. one or more of antimony, arsenic, cadmium, chromium, nickel, selenium, and zirconium) in the sulfuric acid produced from oxidizing the $SO_x$ species, and removing the trace elements from the sulfuric acid by ion exchange. In other embodiments, heavy metal removal may not occur. Yet in other embodiments, heavy metal removal may occur at an off-site location.

After oxidation of the $SO_x$ species in the $SO_x$ absorber 150, gas stream 110b is produced and directed towards the $NO_x$ absorber 160.

The $NO_x$ absorber 160 may be any suitable $NO_x$ absorber that is known in the art. For example, the $NO_x$ absorber 160 may be one that is substantially similar to the one described in U.S. Pat. No. 4,619,608 both in design and reaction conditions. $NO_x$ removal efficiency of about 98% may be achieved by the combination of a gas phase reactor and a $NO_x$ absorber. Since no ammonia is used in the $NO_x$ absorber 160, no ammonia slip occurs. The $NO_x$ absorber 160 may be arranged horizontally or vertically, depending on spatial restrictions or requirements of the system 100. The $NO_x$ absorber 160 may also comprise packed towers or cross-flow vessels that condense and collect nitric acid, hydrochloric acid, as well as heavy metal (e.g. mercury) products.

In the $NO_x$ absorber 160, the gas stream 110b is sprayed with steam to further oxidize the $NO_x$ species. The gas stream 110b may be sprayed with steam at a non-zero angle (e.g. orthogonally). The gas stream 110b may be sprayed with steam at a suitable spraying pressure. Without being bound by theory, it is believed that the following reactions are involved in the removal of $NO_x$ species from gas stream 110b in the $NO_x$ absorber 160:

$$Cl_2 + H_2O \rightarrow HOCl + HCl \qquad 14.$$

$$NOCl + H_2O \rightarrow HNO_2 + HCl \qquad 15.$$

$$NOCl + HOCl + H_2O \rightarrow HNO_3 + 2HCl \qquad 16.$$

$$NO_2Cl + H_2O \rightarrow HNO_2 + HOCl \qquad 17.$$

$$2NO_2 + H_2O \rightarrow HNO_2 + HNO_3 \qquad 18.$$

$$HNO_2 + HOCl \rightarrow HNO_3 + HCl \qquad 19.$$

$$2NO + H_2O + HNO_3 \rightarrow 3HNO_2 \qquad 20.$$

It is believed that the predominant final products of $NO_x$ removal are nitric acid and hydrochloric acid.

The $NO_x$ absorber 160 collects nitric acid having a purity of up to about 99% that may be directed to further processing and/or storage 160" in preparation for commercial shipment and/or sale.

The HCl produced from the oxidation of $NO_x$ species in the gas reactor 140 and the $NO_x$ absorber 160 is collected and directed to an electrolytic unit 160'. At the electrolytic unit 160', the HCl undergoes electrolysis to produce hydrogen gas and chlorine gas. Methods of electrolysing hydrochloric acid are known in the art, and any commercially available electrolytic unit may be used. In a non-limiting example, the electrolytic unit comprises high temperature electrolysis cells.

The hydrogen gas produced from the electrolysis of HCl at electrolytic unit 160' may be re-used in the flue gas treatment system 100. In a non-limiting example, the produced hydrogen gas or a portion thereof is re-directed to the carbon dioxide absorber 180 for use in converting carbon dioxide gas into a hydrocarbon fuel.

The chlorine gas produced from the electrolysis of HCl at electrolytic unit 160' may be re-used in the flue gas treatment system 100. In a non-limiting example, the produced chlorine gas is re-directed towards the reactor 140 and forms the chlorine gas 130 or a part thereof.

Although not shown in FIG. 1, in certain embodiments that gas stream 110b undergoes further heavy metal removal in the $NO_x$ absorber 160 (i.e. removal of any heavy metals that were not removed in the $SO_x$ absorber 150) by a process known in the art such as, but not limited to, the one described in PCT/CA1999/000403. For example, mercury may be converted into a mercury halide (e.g. mercury chloride) which may be collected, sold, or reused, for other downstream applications. In other embodiments, this further heavy metal removal process may not occur.

Gas stream 110c leaving the $NO_x$ absorber 160 is generally removed of $NO_x$ species and consists essentially of water vapour and carbon dioxide gas. Water vapour present in gas stream 110c is removed therefrom by the water vapour remover 170. Such removal may be done by methods known in the art. In a non-limiting example, thermal energy generated from the treatment system 100 (e.g. heat from excess steam, or heat generated specifically for the step of water vapour removal from gas stream 110c) is used to heat the gas stream 110c to evaporate the $H_2O$ content remaining therein, the evaporated $H_2O$ content being collectable downstream. In another non-limiting example, water vapour is removed from gas stream 110c by heat exchangers and the removed water vapour may be collected as steam. Without such treatment or removal step, the water vapour generally would otherwise be vented into the atmosphere.

The collected evaporated $H_2O$ content from gas stream 110c may be condensed into water, and the collected condensed water may be used for other purposes in the flue gas treatment system 100. Such other purposes include, but are not limited to: (i) returning the $H_2O$ content recovered from gas stream 110c to a steam cycle of the flue gas treatment system 100; (ii) re-using the $H_2O$ content recovered from gas stream 110c as process water in the $SO_x$ absorber 150, the $NO_x$ absorber 160, or both the $SO_x$ absorber 150 and the $NO_x$ absorber 160; (iii) using the $H_2O$ content recovered from gas stream 110c to aid in the electrolysis 160' of HCl; and (iv) using the $H_2O$ content recovered from gas stream 110c as a heat source to increase the temperature of the electrolytic reaction of HCl thereby improving the efficiency of said reaction at the electrolytic unit 160'. Such recycling of evaporated $H_2O$ content from flue gas may be desired, particularly for flue gas treatment systems that are situated in locations that experience or are prone to drought or drought-like conditions. It is estimated that, for a 500 MW plant, up to about 750,000 lbs/hr of $H_2O$ content that would otherwise be vented into the atmosphere as steam may be recovered and re-used within the treatment system 100.

Gas stream 110d, which is removed of water vapour, is directed to the carbon dioxide absorber 180 for further processing.

Gas stream 110d consists essentially of carbon dioxide gas. Hydrogen gas produced from the electrolysis of HCl at the electrolytic unit 160' is fed into the carbon dioxide absorber 180, and serves as a reactant required to hydrogenate the carbon dioxide gas in gas stream 110d into methane 112, at the carbon dioxide absorber 180, via the Sabatier process, at industrial scale and economically reasonable costs.

The Sabatier process is catalyzed in the carbon dioxide absorber 180 by an appropriate catalyst such as, but not limited to, a nickel catalyst, ruthenium, alumina, or a copper catalyst. As contemplated in this embodiment, the Sabatier process in the carbon dioxide collector 180 is catalyzed by a copper catalyst, and occurs under atmospheric pressure. As contemplated in this embodiment, the molar feed ratio of $H_2:CO_2$ is greater than or equal to about 3.5:1, and the Sabatier process is carried out at a temperature between about 400° F. and about 700° F. In other embodiments, other suitable reaction parameters may be used.

It is also contemplated in this embodiment (though not shown in FIG. 1) that at least a portion of the water vapour removed from gas stream 110c and the $H_2O$ content collected therefrom undergoes its own electrolytic reaction to generate hydrogen gas and oxygen gas. The hydrogen gas generated from the electrolysis of the collected $H_2O$ content may be directed to the carbon dioxide absorber 180 for use in converting carbon dioxide gas into a hydrocarbon fuel and to further provide the volume of hydrogen gas that is required to hydrogenate the carbon dioxide gas in gas stream 110d into methane 112, at the carbon dioxide absorber 180, via the Sabatier process, at industrial scale and economically reasonable costs. The oxygen gas generated from said electrolysis may be used as a fuel source within the system 100. In other embodiments, the water vapour removed from gas stream 110c and the $H_2O$ content collected therefrom does not undergo further hydrolysis.

Methane 112 produced in the carbon dioxide absorber 180 may be directed downstream for further processing 190. In certain embodiments, methane 112 (or a portion thereof) is compressed (condensed) by methods known in the art to form downstream fuel sources such as, but not limited to, liquefied natural gas (LNG), which may be used (or a portion thereof may be used) as a source of fuel in downstream applications, recycled for use as a fuel source within the system 100, or sold as a product (e.g. as a fuel or chemical feedstock). For example, but without limitation, LNG may be removed from the plant via cryogenic road tanker.

Since methane is combustible without requiring compression or other treatment, in certain embodiments (not shown in FIG. 1) methane 112 (or a portion thereof) may be fed directly into the boiler of the plant, blended and co-fired with the coal, gas or another fossil or hydrocarbon fuel, or may be used as fuel to power a separate turbine, thereby eliminating or reducing the need to store, sequester, or sell the product of condensation (i.e. LNG), while increasing the power output of the plant.

In other non-limiting examples, the methane 112 (or a portion thereof) may be converted to other products such as, but not limited to, a methyl halide. In a non-limiting example, methane 212 (or a portion thereof) is converted to chloromethane through the following reaction, as known in the art:

$$CH_4 + Cl_2 \rightarrow CH_3Cl + HCl \qquad 21.$$

The resulting methyl chloride from Reaction 21 may be further processed into other organic polyhalides, such as dichloro-methane. The resulting methyl chloride may also be converted to other products like methyl alcohols, ethyl alcohols, ethers, aldehydes, ketones, organic acids, esters, amines, and fats and soaps.

EXAMPLE 2

Figure 2:
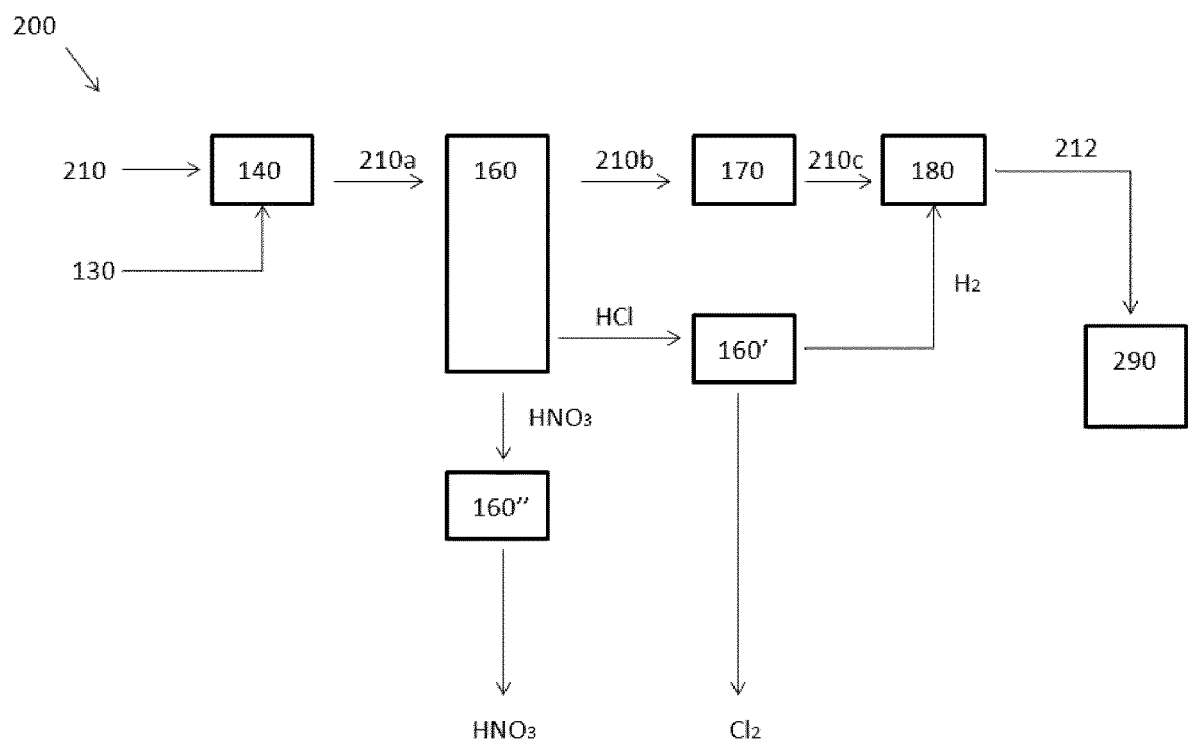
FIG. 2 is a schematic of a flue gas treatment system for use in a gas-burning facility according to another embodiment, the treatment system comprising a gas phase reactor, a NO$_x$ absorber, a water vapour remover, and a carbon dioxide absorber.

Referring to FIG. 2, and according to another embodiment of the present disclosure, there is a flue gas treatment system 200 configured to serve a gas burning facility, the treatment system 200 comprising a gas phase reactor 140, a $NO_x$ absorber 160, a water vapour remover 170, and a carbon dioxide absorber 180. As $SO_x$ species are not generally produced in a gas burning facility, the presence of a $SO_x$ absorber would be optional for a gas burning facility flue gas treatment system.

Flue gas 210 comprises $NO_x$ species, water vapour, and carbon dioxide gas.

Chlorine gas 130 and flue gas 210 are: (i) delivered into the gas phase reactor 140 operating at pre-set reaction conditions such as the reaction conditions described in Example 1; and (ii) mixed in the gas phase reactor 140. For example, the gas phase reactor 140 can be set at a temperature between about 100° C. and about 650° C. Flue gas 210 and chlorine gas 130 mix in the gas phase reactor 140, and the $NO_x$ gas in the flue gas 210 is oxidized generally to nitric acid and hydrochloric acid (see for example Reactions 6 to 12). Gas stream 210a comprising dissolved nitric acid and hydrochloric acid and other pollutants exits the reactor 140 and is directed towards the $NO_x$ absorber 160.

$NO_x$ species that were not removed (e.g. converted) in the reactor 140 are removed from the gas stream 210a in the $NO_x$ absorber 160. Without being bound by theory, it is believed that $NO_x$ species that were not removed in the reactor 140 are removed from the gas stream 210a in the $NO_x$ absorber 160 per reactions 14 to 20 described above in Example 1. It is believed that the predominant final products of $NO_x$ removal are nitric acid and hydrochloric acid.

The $NO_x$ absorber 160 collects nitric acid of a purity up to about 99% that may be directed to further processing and/or storage 160" in preparation for commercial shipment and/or sale.

Although not shown in FIG. 2, in certain optional embodiments, gas stream 210a may undergo heavy metal removal in the $NO_x$ absorber 160 by a process known in the art such as, but not limited to, the one described in PCT/CA1999/000403. In other embodiments, this heavy metal removal process may not occur. Heavy metals are generally not present in a gas plant.

The HCl produced from the oxidation of $NO_x$ species in the gas reactor 140 and the $NO_x$ absorber 160 is collected and directed to an electrolytic unit 160'. At the electrolytic unit 160', the HCl undergoes electrolysis to produce hydrogen gas and chlorine gas. Methods of electrolysing hydrochloric acid are known in the art, and any commercially available electrolytic unit may be used. The hydrogen gas produced from the electrolysis of HCl at electrolytic unit 160' may be re-used in the flue gas treatment system 200. In a non-limiting example, the produced hydrogen gas or a portion thereof is re-directed to the carbon dioxide absorber 180 for use in converting carbon dioxide gas into a hydrocarbon fuel. The chlorine gas produced from the electrolysis of HCl at electrolytic unit 160' may be re-used in the flue gas treatment system 200. In a non-limiting example, the produced chlorine gas is re-directed towards the reactor 140 and forms the chlorine gas 130 or a part thereof.

Gas stream 210b leaving the $NO_x$ absorber 160 is generally removed of $NO_x$ species and consists essentially of water vapour and carbon dioxide gas. Water vapour present in gas stream 210b is removed therefrom by the water vapour remover 170. Such removal may be done by the non-limiting examples described in Example 1.

The collected evaporated $H_2O$ content from gas stream 210b may be condensed into water, and the collected condensed water may be used for other purposes in the flue gas treatment system 200 such as, but not limited to, those described in Example 1. In addition, it is contemplated in this embodiment (though not shown in FIG. 2) that at least a portion of the water vapour removed from gas stream 210b and the $H_2O$ content collected therefrom undergoes its own electrolytic reaction to generate hydrogen gas and oxygen gas. The hydrogen gas generated from the electrolysis of the collected $H_2O$ content may be directed to the carbon dioxide absorber 180 for use in converting carbon dioxide gas into a hydrocarbon fuel. The oxygen gas generated from said electrolysis may be used as a fuel source within the system 200. In other embodiments, the water vapour removed from gas stream 210b and the $H_2O$ content collected therefrom does not undergo further hydrolysis.

Gas stream 210c, which is removed of water vapour, is directed to the carbon dioxide absorber 180 for further processing. Gas stream 210c consists essentially of carbon dioxide gas. Hydrogen gas produced from the electrolysis of HCl at the electrolytic unit 160' is fed into the carbon dioxide absorber 180, and serves as a reactant that is required to hydrogenate the carbon dioxide gas in gas stream 210c into methane 212, at the carbon dioxide absorber 180, via the Sabatier process.

Methane 212 produced in the carbon dioxide absorber 180 may be directed downstream for further processing 290.

In certain embodiments, methane 112 (or a portion thereof) is condensed by methods known in the art to form downstream fuel sources such as, but not limited to, liquefied natural gas (LNG), which may be used (or a portion thereof may be used) as a source of fuel in downstream applications, recycled for use as a fuel source within the system 200, or sold as a product (e.g. as a fuel or chemical feedstock). For example, but without limitation, LNG may be removed from the plant via cryogenic road tanker.

Since methane is combustible without requiring further treatment, in certain embodiments (not shown in FIG. 1) methane 112 or a portion thereof may be used as fuel to generate heat or power a turbine, thereby eliminating or reducing the need to store, sequester, or sell the product of condensation (i.e. LNG), while increasing the power output of the plant.

In addition to conversion to liquefied natural gas as described in Example 1, methane 212 (or a portion thereof) may be rendered into other products. In a non-limiting example, methane 212 (or a portion thereof) is converted to chloromethane using Reaction 21 (as described in Example 1). The resulting methyl chloride from Reaction 21 may be further processed into other organic polyhalides, such as dichloro-methane. The resulting methyl chloride may also be converted to other products like methyl alcohols, ethyl alcohols, ethers, aldehydes, ketones, organic acids, esters, amines, and fats and soaps.

While Examples 1 and 2 above describe the water vapour remover 170 and the carbon dioxide absorber 180 as separate units, in other embodiments and examples, the water vapour remover and the carbon dioxide absorber may be combined as one unit. In a non-limiting example, heat exchangers are placed around the carbon dioxide absorber to evaporate the water vapour from the gas stream prior to reacting the carbon dioxide gas remaining in the gas stream with hydrogen gas. In another non-limiting example, steam from the system is passed over the carbon dioxide absorber to evaporate the water vapour from the gas stream prior to reacting the carbon dioxide gas remaining in the gas stream with hydrogen gas.

It is understood that the embodiments presented in the disclosure are non-limiting examples of flue gas treatment systems contemplated in this disclosure. While in the embodiments only one clean-up unit (e.g. a $SO_x$ absorber, a $NO_x$ absorber, a carbon dioxide absorber, a Sabatier reactor, etc.) is described for each targeted flue gas pollutant, other embodiments may contemplate one or more clean-up units per targeted flue gas pollutant. For example, a treatment system may comprise one or more gas phase reactors connected in series, one or more $SO_x$ absorbers connected in series, one or more $NO_x$ absorbers connected in series, one or more water vapour removers connected in series, one or more $H_2O$ electrolytic units connected in series, one or more HCl electrolytic units connected in series, and/or one or more carbon dioxide absorbers connected in series. Having one or more of the same clean-up units arranged in series may improve the collection and removal of certain flue gas pollutants. For example, since the volumes of carbon dioxide in the flue gas are much greater than the volumes of $SO_x$ and $NO_x$ species in the flue gas, additional carbon dioxide absorbers connected in series may be beneficial in order to adequately remove the carbon dioxide from the flue gas by converting it, for example by the Sabatier process, into, for example, a hydrocarbon fuel for use in downstream applications.

All citations herein, and all documents cited in the cited documents, are hereby incorporated by reference.

It is contemplated that any part of any aspect or embodiment discussed in this specification can be implemented or combined with any part of any other aspect or embodiment discussed in this specification. While particular embodiments have been described in the foregoing, it is to be understood that other embodiments are possible and are intended to be included herein. It will be clear to any person skilled in the art that modification of and adjustment to the foregoing embodiments, not shown, is possible. Accordingly, the scope of the claims should not be limited by the preferred embodiments set forth in the examples, but should be given the broadest interpretation consistent with the description as a whole.

REFERENCES

[1] Patel, S., The Big Picture: Energy for Power, *Power*, April 2016, p. 12.
[2] Patel, S., The Big Picture: Future Coal Fleet, *Power*, January 2016, p. 10.
[3] Environmental Defense Fund, Coal-fired Power Plants are Big Contributors to Sooty Particle Pollution in Eastern States, 2008.
[4] Bemand, P. P. et al., *J. Chem. Soc. Faraday Trans.* 1, 1973, 69: 1356.
[5] Water Vapor, NOAA National Centers for Environmental Information, https://www.ncdc.noaa.gov/monitoring-references/faq/greenhouse-gases.php, accessed Dec. 14, 2016.
[6] Ralston, J., The Sabatier Reaction, Possible Sources of CO2 Emissions, Mar. 4, 2010, http://www.pennenergy.com/articles/pennenergy/2010/03/the-sabatier-reaction.html, accessed Dec. 14, 2016.
[7] Lunde, P. J et al., *Ind. Eng. Chem. Process Des. Dev.*, 1974, 13(1): 27-33.

What is claimed is:

1. A system comprising:
   (a) a gas phase oxidation (GPO) reactor configured to receive a flue gas stream comprising $NO_x$ species and carbon dioxide gas, the GPO reactor further configured to receive chlorine gas, liquid or solution, and to oxidize the $NO_x$ species in the flue gas stream to produce a gas stream comprising nitric acid and hydrochloric acid, wherein the GPO reactor is configured to receive a chlorine gas stream;
   (b) an electrolytic unit configured to receive the hydrochloric acid and configured to electrolyse the hydrochloric acid to produce hydrogen gas and chlorine gas, optionally wherein at least a portion of the chlorine gas produced in the electrolytic unit is recycled into the GPO reactor; and
   (c) a Sabatier reactor configured to receive both a gas stream, downstream from the GPO reactor, and at least a portion of the hydrogen gas from the electrolytic unit, the Sabatier reactor further configured to hydrogenate the carbon dioxide gas in the gas stream into a hydrocarbon fuel comprising methane.

2. The system according to claim 1, further comprising a $NO_x$ absorber configured to receive a gas stream from (a) or downstream from (a), the $NO_x$ absorber further configured to oxidize and collect the $NO_x$ species remaining in the gas stream, wherein the system is further configured to direct at least a portion of hydrochloric acid from the $NO_x$ absorber to the electrolytic unit, optionally wherein the $NO_x$ absorber is configured in series between the GPO reactor and the Sabatier reactor.

3. The system according to claim 1, wherein the flue gas further comprises $SO_x$ species, and wherein the system further comprises a $SO_x$ absorber configured to receive a gas stream from (a) or downstream from (a), and further configured to oxidize and collect the $SO_x$ species in the gas stream as sulfuric acid.

4. The system according to claim 2, wherein the flue gas further comprises $SO_x$ species, and wherein the system further comprises a $SO_x$ absorber configured in series between the GPO reactor and the $NO_x$ absorber, the $SO_x$ absorber configured to receive a gas stream from (a) or downstream from (a), and further configured to oxidize and collect the $SO_x$ species in the gas stream as sulfuric acid, optionally: wherein the flue gas further comprises mercury and/or at least one heavy metal trace element and the $SO_x$ absorber is further configured to remove the mercury and/or the at least one heavy metal trace element.

5. The system according to claim 3, wherein the flue gas further comprises mercury and/or at least one heavy metal trace element, and wherein the $SO_x$ absorber is further configured to remove the mercury and/or the at least one heavy metal trace element.

6. The system according to claim 1, wherein the flue gas further comprises water vapour, and wherein the system further comprises a water vapour remover configured to remove the water vapour from the gas stream before (c), optionally wherein the water vapour remover is configured in parallel to the electrolytic unit.

7. The system according to claim 2, wherein the flue gas further comprises water vapour, and wherein the system further comprises a water vapour remover configured in series between the $NO_x$ absorber and the Sabatier reactor, optionally wherein the water vapour remover is configured in parallel to the electrolytic unit.

8. The system according to claim 1, wherein the Sabatier reactor uses a catalyst selected from the group consisting of a nickel catalyst, a ruthenium catalyst, an alumina catalyst, and a copper catalyst, optionally wherein the catalyst is the copper catalyst.

9. The system according to claim 1, further configured to direct the methane to a boiler or combustion chamber for combustion of the methane to generate heat or power.

10. The system according to claim 1, further comprising a compressor configured to condense liquefied natural gas from the methane.

11. A method of producing a hydrocarbon fuel, comprising methane, from a flue gas stream comprising $NO_x$ species, water vapour, and carbon dioxide gas, the method comprising:
  (a) generating hydroxyl radicals and chlorine radicals;
  (b) oxidizing the $NO_x$ species in the gas stream with the hydroxyl radicals and chlorine radicals to produce a gas stream comprising nitric acid and hydrochloric acid, water vapour and carbon dioxide gas;
  (c) removing the water vapour from the gas stream to produce a dehydrated gas stream;
  (d) producing hydrogen gas from electrolyzing the hydrochloric acid produced in (b), and optionally from electrolyzing the water vapour removed from the gas stream in (c); and
  (e) using a Sabatier reaction to hydrogenate the carbon dioxide gas in the dehydrated gas stream from (c) with the hydrogen gas produced in (d) to produce the hydrocarbon fuel.

12. The method according to claim 11, wherein the flue gas stream further comprises $SO_x$ species, and wherein the method further comprises oxidizing the $SO_x$ species to produce sulfuric acid, and removing the sulfuric acid from the gas stream to produce a gas stream that is substantially free of $SO_x$ species.

13. The method according to claim 12, wherein the flue gas stream further comprises trace elements selected from a group consisting of antimony, arsenic, cadmium, chromium, nickel, selenium, zirconium, and any combination thereof, and wherein the method further comprises removing the trace elements from the gas stream by capturing the trace elements in the sulfuric acid, and wherein the method optionally further comprises removing the trace elements from the sulfuric acid by ion exchange.

14. The method according to claim 12, the flue gas stream further comprising mercury, and wherein the method further comprises removing the mercury from the gas stream, wherein removing the mercury optionally comprises converting the mercury to $HgCl_2$ and capturing the $HgCl_2$ in the sulfuric acid, and wherein the method optionally further comprises recovering the mercury from the sulfuric acid.

15. The method according to claim 11, further comprising further oxidizing the $NO_x$ species with steam to produce hydrochloric acid and a gas stream that is substantially free of $NO_x$ species.

16. The method according to claim 15, further comprising using chlorine gas produced from (d) to generate at least some of the chlorine radicals in (a).

17. The method according to claim 11, wherein (d) comprises electrolyzing the water vapour removed from the gas stream in (c), the electrolyzing of the water vapour also producing oxygen gas, and wherein the method optionally further comprises directing the oxygen gas from (d) to aid in combustion of a fuel to generate heat or power.

18. The method according to claim 11, wherein the Sabatier reaction is catalysed by a catalyst selected from the group consisting of a nickel catalyst, a ruthenium catalyst, an alumina catalyst, and a copper catalyst.

19. The method according to claim 11, further comprising compressing the methane to reduce the volume of the methane or condensing the methane to produce liquefied natural gas.

20. The method according to claim 11, further comprising combusting the methane to generate heat or power, optionally wherein the methane is blended and co-fired with another hydrocarbon fuel that is optionally selected from coal or gas.

* * * * *